US010310600B2

(12) United States Patent
Hong et al.

(10) Patent No.: US 10,310,600 B2
(45) Date of Patent: Jun. 4, 2019

(54) DISPLAY APPARATUS, VEHICLE AND DISPLAY METHOD

(71) Applicant: HYUNDAI MOTOR COMPANY, Seoul (KR)

(72) Inventors: Gi Beom Hong, Bucheon-si (KR); Jungsang Min, Seoul (KR)

(73) Assignee: Hyundai Motor Company, Seoul (KR)

(*) Notice: Subject to any disclaimer, the term of this patent is extended or adjusted under 35 U.S.C. 154(b) by 0 days.

(21) Appl. No.: 14/932,921

(22) Filed: Nov. 4, 2015

(65) Prior Publication Data

US 2016/0282940 A1 Sep. 29, 2016

(30) Foreign Application Priority Data

Mar. 23, 2015 (KR) .................... 10-2015-0040322

(51) Int. Cl.
*G06F 3/01* (2006.01)
*A61B 5/0484* (2006.01)
(Continued)

(52) U.S. Cl.
CPC .......... *G06F 3/015* (2013.01); *A61B 5/04842* (2013.01); *B60K 35/00* (2013.01);
(Continued)

(58) Field of Classification Search
CPC . G06F 3/015; G06F 3/013; G06F 3/16; G06F 3/1446; B60K 35/00;
(Continued)

(56) References Cited

U.S. PATENT DOCUMENTS 5,521,580 A * 5/1996 Kaneko ................. B60K 28/02
180/272
6,575,902 B1 * 6/2003 Burton ..................... A61B 5/18
600/300
(Continued)

FOREIGN PATENT DOCUMENTS

JP          4287903 B2    7/2009
JP       2010-057658 A    3/2010
(Continued)

OTHER PUBLICATIONS

Korean Office Action issued in Korean Application No. 10-2015-0040322 dated Jul. 21, 2016, with English Translation.
(Continued)

*Primary Examiner* — Jose R Soto Lopez
(74) *Attorney, Agent, or Firm* — Morgan Lewis & Bockius LLP

(57) ABSTRACT

A display apparatus, a vehicle, and a display method are disclosed, which recognize the user's intention by recognizing the user's eyes, and apply the recognized result to a device control process, thereby greatly increasing convenience of the input unit manipulation actions of the user. A display apparatus includes: a controller configured to insert a visual stimulus signal into basic visual information according to a predetermined frequency; a display unit configured to display the visual stimulus signal for generating an electroencephalogram (EEG) signal and the basic visual information; and an EEG analyzer configured to determine a frequency occupied by the generated EEG signal.

26 Claims, 35 Drawing Sheets

(51) Int. Cl.
*B60K 35/00* (2006.01)
*G02B 27/01* (2006.01)
*G06F 3/14* (2006.01)
*G06F 3/16* (2006.01)
*A61B 5/048* (2006.01)
*A61B 5/18* (2006.01)
*B60K 28/00* (2006.01)

(52) U.S. Cl.
CPC ......... *G02B 27/0101* (2013.01); *G06F 3/013* (2013.01); *G06F 3/1446* (2013.01); *G06F 3/16* (2013.01); *A61B 5/048* (2013.01); *A61B 5/18* (2013.01); *B60K 28/00* (2013.01); *B60K 2350/106* (2013.01); *B60K 2350/2056* (2013.01); *G02B 2027/014* (2013.01)

(58) Field of Classification Search
CPC ...... B60K 2350/106; B60K 2350/2056; B60K 28/00; G02B 27/0101; G02B 2027/014; A61B 5/04842; A61B 5/048; A61B 5/18
See application file for complete search history.

(56) References Cited

U.S. PATENT DOCUMENTS

| | | | | |
|---|---|---|---|---|
| 9,116,600 | B2* | 8/2015 | Gonsalves | G06F 3/0482 |
| 9,823,744 | B2* | 11/2017 | Publicover | G06F 21/64 |
| 2007/0164990 | A1* | 7/2007 | Bjorklund | G06F 3/017 |
| | | | | 345/156 |
| 2008/0158436 | A1* | 7/2008 | Chao | G06F 3/0325 |
| | | | | 348/734 |
| 2009/0187114 | A1* | 7/2009 | Morikawa | G06F 3/015 |
| | | | | 600/545 |
| 2009/0247895 | A1* | 10/2009 | Morikawa | A61B 5/04842 |
| | | | | 600/544 |
| 2009/0270753 | A1* | 10/2009 | Adachi | A61B 5/0476 |
| | | | | 600/544 |
| 2010/0050128 | A1* | 2/2010 | Chiang | G06F 9/451 |
| | | | | 715/847 |
| 2010/0130882 | A1* | 5/2010 | Nakada | A61B 5/04842 |
| | | | | 600/544 |
| 2010/0186031 | A1* | 7/2010 | Pradeep | A61B 5/04842 |
| | | | | 725/34 |
| 2010/0249532 | A1* | 9/2010 | Maddess | A61B 5/04842 |
| | | | | 600/300 |
| 2011/0066928 | A1* | 3/2011 | Karlsson | G06F 3/04815 |
| | | | | 715/202 |
| 2012/0025969 | A1* | 2/2012 | Dozza | B60Q 1/44 |
| | | | | 340/463 |
| 2012/0229385 | A1* | 9/2012 | Fu | G06F 3/0346 |
| | | | | 345/163 |
| 2012/0249614 | A1* | 10/2012 | Lee | A61B 5/0482 |
| | | | | 345/691 |
| 2013/0100010 | A1* | 4/2013 | Lee | G06F 3/015 |
| | | | | 345/156 |
| 2013/0127708 | A1* | 5/2013 | Jung | A61B 5/0006 |
| | | | | 345/156 |
| 2013/0130799 | A1* | 5/2013 | Van Hulle | A61B 5/04842 |
| | | | | 463/36 |
| 2013/0138248 | A1* | 5/2013 | Mathan | A61B 5/04842 |
| | | | | 700/258 |
| 2013/0144184 | A1* | 6/2013 | Regini | A61B 5/04842 |
| | | | | 600/558 |
| 2013/0283199 | A1* | 10/2013 | Selig | G06F 3/0484 |
| | | | | 715/781 |
| 2014/0058483 | A1* | 2/2014 | Zao | A61N 5/06 |
| | | | | 607/88 |
| 2014/0119711 | A1* | 5/2014 | Nyhed | H04N 5/772 |
| | | | | 386/241 |
| 2015/0062353 | A1* | 3/2015 | Dalal | G11B 27/3036 |
| | | | | 348/194 |
| 2015/0182843 | A1* | 7/2015 | Esposito | G06K 9/00342 |
| | | | | 700/91 |
| 2015/0253573 | A1* | 9/2015 | Sako | G02B 27/0172 |
| | | | | 345/156 |
| 2016/0048979 | A1* | 2/2016 | Xu | G06F 3/04817 |
| | | | | 345/592 |
| 2016/0124625 | A1* | 5/2016 | Lawton | H04N 21/4312 |
| | | | | 715/800 |
| 2016/0207455 | A1* | 7/2016 | Kim | B60K 28/066 |
| 2016/0214467 | A1* | 7/2016 | El Idrissi | B60J 3/04 |
| 2016/0235323 | A1* | 8/2016 | Tadi | A61B 5/7285 |
| 2017/0123492 | A1* | 5/2017 | Marggraff | G06F 3/0236 |
| 2017/0279957 | A1* | 9/2017 | Abramson et al. | H04M 1/72577 |

FOREIGN PATENT DOCUMENTS

| | | | |
|---|---|---|---|
| JP | 2010057658 A | * | 3/2010 |
| JP | 2011-086125 A | | 4/2011 |
| JP | 2011086125 A | * | 4/2011 |
| JP | 2011086125 A | * | 4/2011 |
| JP | 2012-128512 A | | 7/2012 |
| JP | 2013-027438 A | | 2/2013 |
| KR | 10-2010-0009304 A | | 1/2010 |
| KR | 10-2012-0075672 A | | 7/2012 |
| KR | 10-2013-0061076 A | | 6/2013 |
| KR | 2013-0108778 A | | 10/2013 |
| KR | 10-2014-0011204 A | | 1/2014 |
| KR | 10-2014-0129820 A | | 11/2014 |

OTHER PUBLICATIONS

Extended European Search Report issued in European Application No. 16161805.3 dated Jul. 20, 2016.
Korean Office Action issued in corresponding Korean Patent Application No. 10-2015-0040322, dated Jan. 8, 2016.

* cited by examiner

VISUAL STIMULUS PATTERN

VISUAL STIMULUS PATTERN

200

DISPLAY APPARATUS, VEHICLE AND DISPLAY METHOD

CROSS-REFERENCE TO RELATED APPLICATION

This application claims the benefit of Korean Patent Application No. 10-2015-0040322, filed on Mar. 23, 2015 in the Korean Intellectual Property Office, the disclosure of which is incorporated herein by reference.

TECHNICAL FIELD

Embodiments of the present invention relate to a display apparatus, a vehicle and a display method, which can recognize user's eyes and provide feedback for the recognized user's eyes.

BACKGROUND

In general, in order to allow a user to control a device as well as to obtain necessary information, the user has to directly manipulate an input unit by hand. However, if the user currently drives a vehicle or cannot freely use his or her hands, the user may have difficulty in manipulating the input unit and unexpected troubles may occur in other tasks such as vehicle driving.

Therefore, a technology for recognizing the user's intention while simultaneously minimizing the number of manipulation times of the input unit, and controlling a device or providing necessary information on the basis of the recognized result needs to be developed.

Recently, many developers and companies have been conducting intensive research into a technology for recognizing the user's intention by recognizing the user's eyes. Assuming that the technology is applied to a device control method, all or some of the input unit manipulation operations can be replaced with a behavior of the user who gazes at a specific region instead of directly operating the input unit, such that the user can more conveniently control the corresponding device and can easily obtain desired information from the device.

SUMMARY

Therefore, it is an aspect of the present invention to provide a display apparatus, a vehicle, and a display method, which recognize the user's intention by recognizing the user's eyes, and apply the recognized result to a device control process, thereby greatly increasing convenience of the input unit manipulation actions of the user.

Additional aspects of the invention will be set forth in part in the description which follows and, in part, will be obvious from the description, or may be learned by practice of the invention.

In accordance with an aspect of the present invention, a display apparatus includes: a controller configured to insert a visual stimulus signal into basic visual information according to a predetermined frequency; a display unit configured to display the visual stimulus signal for generating an electroencephalogram (EEG) signal and the basic visual information; and an electroencephalogram (EEG) analyzer configured to determine a frequency occupied by the generated EEG signal.

The EEG signal generated by the visual stimulus signal may include a steady-state visual evoked potential (SSVEP).

The display unit may display the basic visual information in a form of moving images or still images.

If the basic visual information is displayed in the form of moving images, the controller may insert the visual stimulus signal at a specific time at which a frame constructing the moving images is not displayed.

The display apparatus may further include: a communication unit configured to receive the generated EEG signal from an electroencephalogram (EEG) detector for detecting the EEG signal of a user.

The controller may generate a control signal to activate a function corresponding to the frequency occupied by the generated EEG signal is performed.

The controller may divide a screen image of the display unit into a plurality of regions, and insert visual stimulus signals having different frequencies into basic visual information displayed on the divided regions.

The EEG analyzer may recognize the user's eyes on the basis of the frequency occupied by the generated EEG signal.

In accordance with another aspect of the present invention, a vehicle includes: a controller configured to insert a visual stimulus signal into basic visual information according to a predetermined frequency; a display unit configured to display the visual stimulus signal for generating an electroencephalogram (EEG) signal and the basic visual information; a communication unit configured to receive an EEG signal from an EEG detector for detecting an EEG signal of a user; and an electroencephalogram (EEG) analyzer configured to determine a frequency occupied by the EEG signal of the user, and determine a region gazed by the user on the basis of the determined frequency.

The electroencephalogram (EEG) signal generated by the visual stimulus signal may include a steady-state visual evoked potential (SSVEP).

The display unit may include a plurality of displays.

The display unit may include an Audio Video Navigation (AVN) display, a cluster display, and a head-up display.

The controller may insert visual stimulus signals having different frequencies into basic visual information respectively displayed on the plurality of displays.

The controller may control a function related to the display gazed by the user from among the plurality of displays.

The vehicle may further include an input unit configured to receive a control command from the user. The controller may control a function related to the user-gazed display according to a control command received from the input unit manipulated by the user.

The controller may insert different visual stimulus signals into visual information displayed on different regions of the display unit.

If the user gazes at one of the regions of the display unit, the controller may immediately execute a function corresponding to the one of the regions, such that the immediately executed function may be determined to be a shortcut function.

The vehicle may further include a speaker configured to output an acoustic or sound signal.

If the user gazes at the display unit during a predetermined reference time or more, the controller may output a warning message through at least one of the display unit and the speaker.

If the user does not gaze at traffic lights, the controller may output a warning message through at least one of the display unit and the speaker.

If the user gazes at a red light from among traffic lights, and if the vehicle does not stop driving, the controller may output a warning message through at least one of the display unit and the speaker.

The display unit may enlarge a display size of a region corresponding to a function frequently used by the user or a display size of a region frequently gazed by the user.

The controller may determine the function frequently used by the user or the function frequently gazed by the user to be the shortcut function.

In accordance with another aspect of the present invention, a display apparatus includes: a controller configured to insert a visual stimulus signal into basic visual information according to a predetermined frequency; and a display unit configured to display the visual stimulus signal for generating an electroencephalogram (EEG) signal and the basic visual information.

In accordance with another aspect of the present invention, a vehicle for receiving an electroencephalogram (EEG) signal of a user who gazes at an advertisement display device that displays not only basic visual information but also a visual stimulus signal inserted into the basic visual information according to a predetermined frequency, includes: an EEG analyzer configured to determine a frequency occupied by the EEG signal of the user, and determine a region gazed by the user on the basis of the determined frequency; and a controller, if the user-gazed region is the advertisement display device, configured to provide information associated with the advertisement display device through a display unit or an output unit.

The display unit may include an Audio Video Navigation (AVN) display, a cluster display, and a head-up display.

The head-up display may display information associated with the advertisement display device using an augmented reality technology.

In accordance with another aspect of the present invention, a display method includes: inserting a visual stimulus signal into basic visual information according to a predetermined frequency; receiving an electroencephalogram (EEG) signal of a user; determining a region gazed by the user by analyzing the received EEG signal; and performing a control function corresponding to the user-gazed region.

The determining the user-gazed region may include: determining a frequency occupied by the received EEG signal; and determining whether the determined frequency is identical to the predetermined frequency of the visual stimulus signal.

The display method may further include: mapping a region on which the visual stimulus signal is displayed to a control function corresponding to the region, and storing the mapped result.

BRIEF DESCRIPTION OF THE DRAWINGS

These and/or other aspects of the invention will become apparent and more readily appreciated from the following description of the embodiments, taken in conjunction with the accompanying drawings of which.

DETAILED DESCRIPTION

Figure 1:
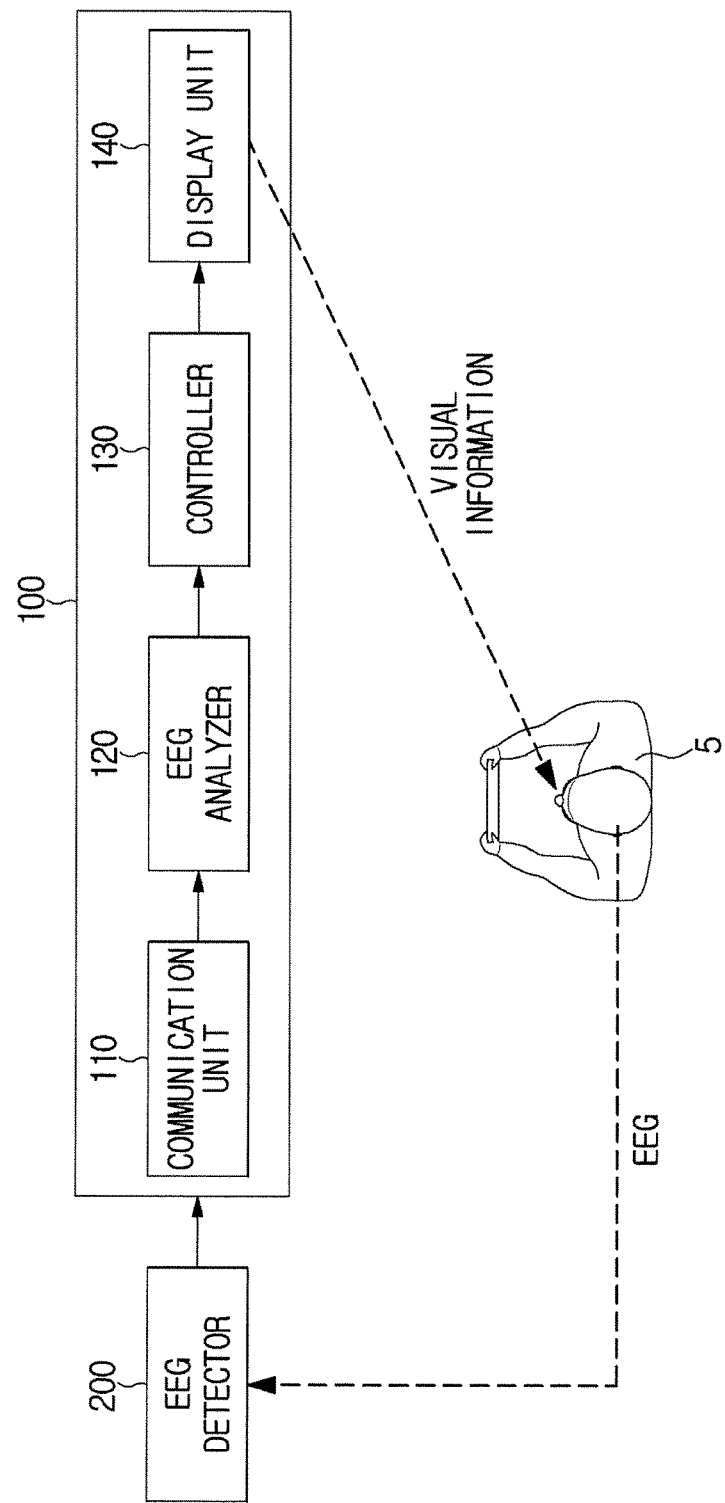
FIG. 1 is a block diagram illustrating a display apparatus according to an embodiment of the present invention.

Reference will now be made in detail to the embodiments of the present invention, examples of which are illustrated in the accompanying drawings, wherein like reference numerals refer to like elements throughout. A display apparatus, a vehicle, and a display control method according to embodiments of the present invention will hereinafter be described with reference to FIG. 1.

FIG. 1 is a block diagram illustrating a display apparatus according to an embodiment of the present invention.

Referring to FIG. 1, a display apparatus 100 according to an embodiment includes a display unit 140 configured to provide a user with visual information, a controller 130 configured to control the display unit 140, a communication unit 110 to receive an electroencephalogram (EEG) signal from an EEG detector 200 having detected an EEG signal of a user who receives visual information, and an EEG analyzer 120 configured to recognize the user's intention by analyzing the received EEG signal.

The display apparatus 100 can recognize the user's intention by recognizing the user's eyes in such a manner that the number of physical manipulation times of the input unit serving as an interface device between a user and a device can be minimized and the display apparatus 100 can be controlled using a minimum number of manipulation times of the input unit.

In order to correctly recognize the user's eyes, the display apparatus 100 may measure and analyze an electroencephalogram (EEG) signal of the user. The EEG signal is a potential obtained when fine brain-scalp signals acquired by synthesizing electrical signals generated from brain nerves are measured using an electrode. In more detail, a steady-state visual evoked potential (SSVEP) can be used. SSVEP is an EEG signal derived from the vicinity of the occipital lobe taking charge of a visual region of the brain when the user gazes at a visual stimulus signal having a constant frequency. Since SSVEP has the same frequency component as that of the visual stimulus signal, the frequency of the visual stimulus signal applied to the user is compared with the frequency of an EEG signal of the user, so that it can be determined whether the user gazes at the corresponding visual stimulus signal.

In order to recognize the user's eyes using SSVEP, the controller 130 may control the display unit 140 to display visual information including a visual stimulus signal having a predetermined frequency. In this case, information regarding the predetermined frequency needs to be pre-stored in the display apparatus 100, but the size of the frequency is not limited.

If the EEG detector 200 detects an EEG signal of the user and transmits the EEG signal to the display apparatus 100, the communication unit 100 receives the EEG signal and transmits the received EEG signal to the EEG analyzer 120.

Although the embodiment has disclosed that the EEG detector 200 is spaced apart from the display apparatus 100 for convenience of description, it should be noted that the EEG detector 200 may also be contained in the display apparatus 100.

The EEG analyzer 120 may determine whether the user EEG signal detected by the EEG detector 200 has a specific frequency. The specific frequency means the predetermined frequency. For this purpose, various analysis methods can be used. For example, a power spectral density analysis method or a canonical correlation analysis method may be used. In addition, pre-processing such as amplification or filtering may be carried out prior to analyzing the EEG signal, and as such a detailed description thereof will hereinafter be given in detail.

The controller 130 may perform a control process for the analysis result of the EEG signal. For example, if the user's gaze corresponds to a control process of the display unit 140, the controller 130 may control the display unit 140 to display a screen image desired by the user. If the user's gaze corresponds to a control process of other devices, the controller 130 may transmit a control signal to the corresponding device. A detailed control operation based on the EEG analysis result will hereinafter be described.

Figure 2:
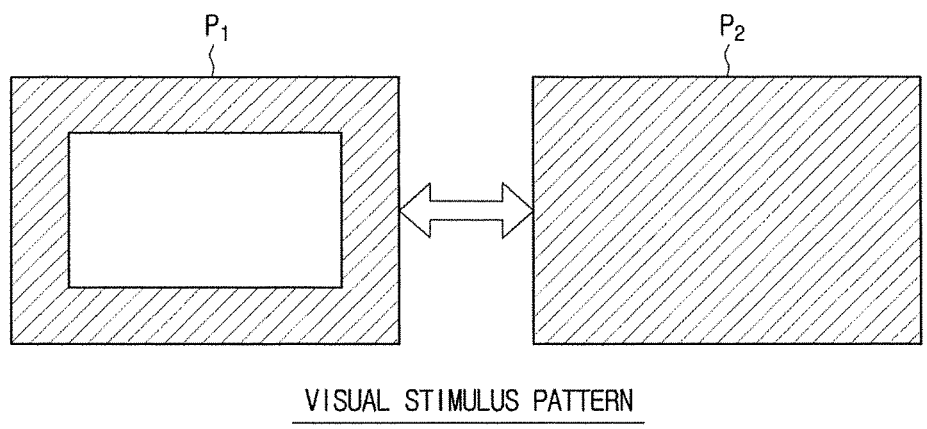
FIGS. 2 and 3 illustrate exemplary visual stimulus signals displayed on a display apparatus according to an embodiment of the present invention.
Figure 3:
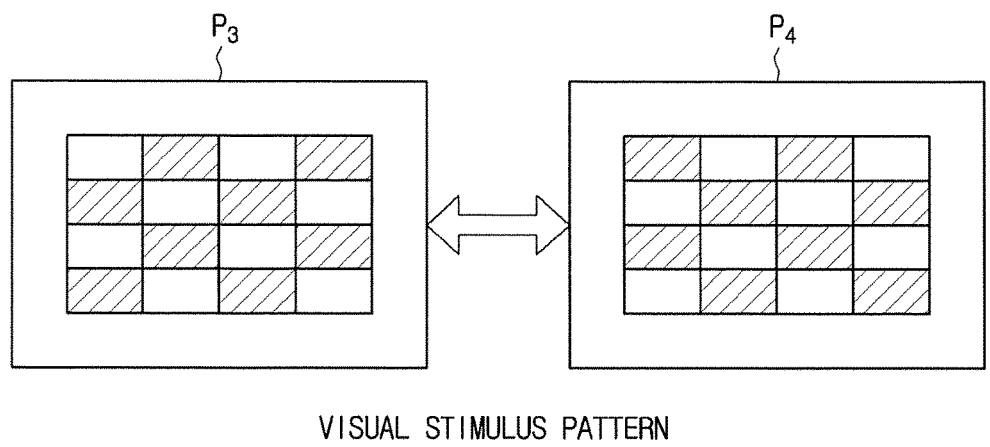

FIGS. 2 and 3 illustrate exemplary visual stimulus signals displayed on a display apparatus according to an embodiment of the present invention.

As described above, the controller 130 may control the display unit 140 to display visual information including a visual stimulus signal having a specific frequency. SSVEP may be generated by the photic driving response. The photic driving response of a brain indicates that, when the user intensively gazes at a pattern or flash that is blinking at a specific frequency, the same frequency is measured at the occipital lobe visual cortex.

As a representative example of the visual stimulus pattern used to generate the visual stimulus signal having a specific frequency, a first pattern ($P_1$) having a rectangular pattern and a second pattern ($P_2$) having no rectangular pattern may cross each other as shown in FIG. 2, or third and fourth patterns ($P_3$, $P_4$) having different check patterns may cross each other as shown in FIG. 3, resulting in formation of a frequency. However, the visual stimulus patterns shown in FIGS. 2 and 3 are merely examples for allowing the display apparatus 100 to generate the visual stimulus signal having a specific frequency, and the scope or spirit of the display apparatus 100 of the present invention is not limited thereto.

Figure 4:
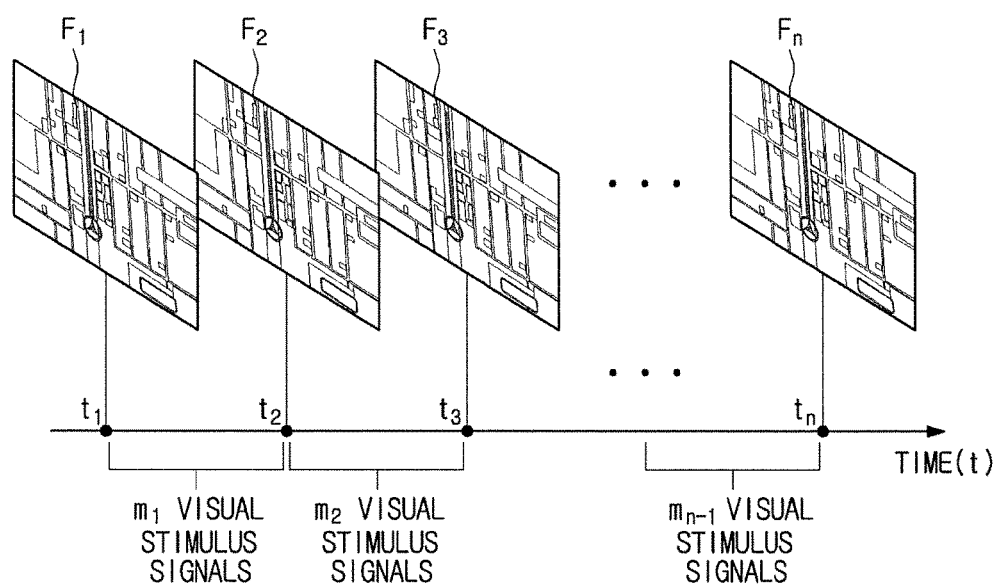
FIGS. 4 to 6 illustrate exemplary insertion formats of a visual stimulus signal that has a specific frequency and is inserted between basic visual information frames.
Figure 5:
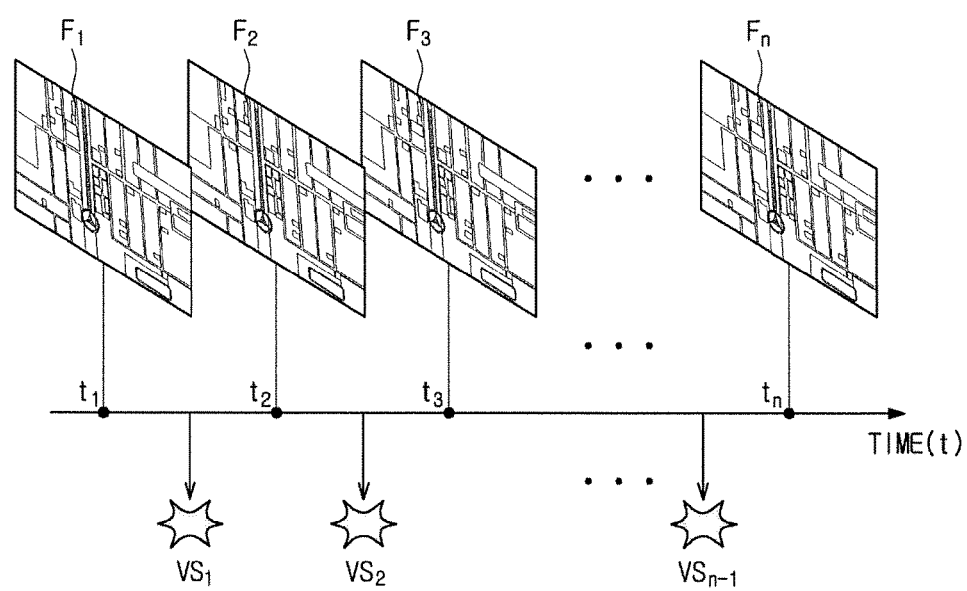
Figure 6:
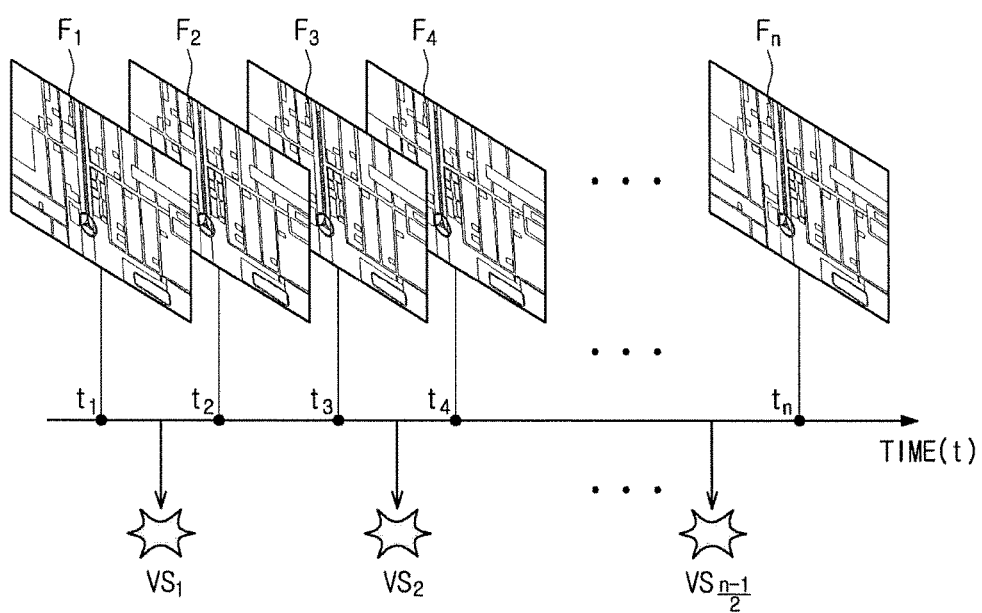

FIGS. 4 to 6 illustrate exemplary insertion formats of a visual stimulus signal that has a specific frequency and is inserted between basic visual information frames.

Visual information displayed on the display unit 140 may include a visual stimulus signal for generating the EEG signal and the basic visual information. The controller 130 may insert the visual stimulus signal for generating the EEG signal into the basic visual information displayed on the display unit 140. The basic visual information may be displayed on the display unit 140 so as to provide the user with information or content. The basic visual information may generate the EEG signal having a specific frequency in such a manner that the basic visual information can be distinguished from the visual stimulus signal used to recognize the user's intention. For example, the basic visual information may include navigation screen image information, audio screen image information, video screen image information, etc.

In addition, the basic visual information may be a moving image or a still image. If the basic visual information is the moving image, a visual stimulus signal may be inserted between frames constructing the moving image, i.e., the visual stimulus signal may be inserted into a time at which no frames are displayed or into a section in which no frames are displayed. If the basic visual information is the still image, the visual stimulus signal may be inserted into a time in which the still image is successively displayed. Alternatively, the still image may be displayed according to a predetermined frame rate in the same manner as in the moving image, and the visual stimulus signal may also be inserted between the still image frames as necessary.

As shown in FIG. 4, if the moving images are displayed at a frame rate (i.e., nFPS) for displaying n frames per second on the display unit 140, the controller 130 may insert the visual stimulus signal for generating the EEG signal between individual frames ($F_1$, $F_2$, $F_3$, ..., $F_n$). In more detail, $m_1$ visual stimulus signals may be inserted between a display time ($t_1$) of a first frame ($F_1$) and a display time ($t_2$) of second frame ($F_2$), and $m_2$ visual stimulus signals may be inserted between a display time ($t_2$) of a second frame ($F_2$) and a display time ($t_3$) of a third frame ($F_3$). Likewise, the visual stimulus signal may also be inserted between the remaining times, and $m_{n-1}$ visual stimulus signals may be inserted between a display time of the (n−1)-th frame and a display time ($t_n$) of the n-th frame. In this case, $m_1 \sim m_{n-1}$ may be integers equal to or higher than zero '0', and may have the same value or different values.

The controller 130 may adjust the number ($m_1 \sim m_{n-1}$) of visual stimulus signals inserted into individual frames such that it can make a desired frequency.

For example, as shown in FIG. 5, each of $m_1 \sim m_{n-1}$ may be assigned '1'. In more detail, if one visual stimulus signal is inserted between all frames, (n−1) visual stimulus signals ($VS_1$, $VS_2$, ... $VS_{n-1}$) per second may be displayed. In this case, a frequency of the visual stimulus signal displayed on the display unit 140 may be set to (n−1)Hz.

In another example, as shown in FIG. 6, a single visual stimulus signal is inserted between a first time ($t_1$) for displaying a first frame ($F_1$) and a second time ($t_2$) for displaying a second frame ($F_2$), and no visual stimulus signal is inserted between the second time ($t_2$) for displaying the second frame ($F_2$) and a third time ($t_3$) for displaying a third frame ($F_3$) in such a manner that the visual stimulus signal may be inserted alternately. In this case, (n−1)/2 (where n is an odd number) visual stimulus signals ($VS_1$, $VS_2$, ..., $VS_{(n-1)/2}$) may be displayed for one second, and the frequency of each visual stimulus signal displayed on the display unit 140 may be set to (n−1)/2 Hz.

As described above, the controller 130 controls basic visual information (i.e., a TV program, a movie, a navigation screen image, etc. desired by the user) to be displayed without change, and at the same time inserts a visual stimulus signal into the basic visual information during a momentary time incapable of being recognized by the user, such that the controller 130 can efficiently use the display without causing eye fatigue or user inconvenience, and can recognize the user's eyes.

Figure 7:
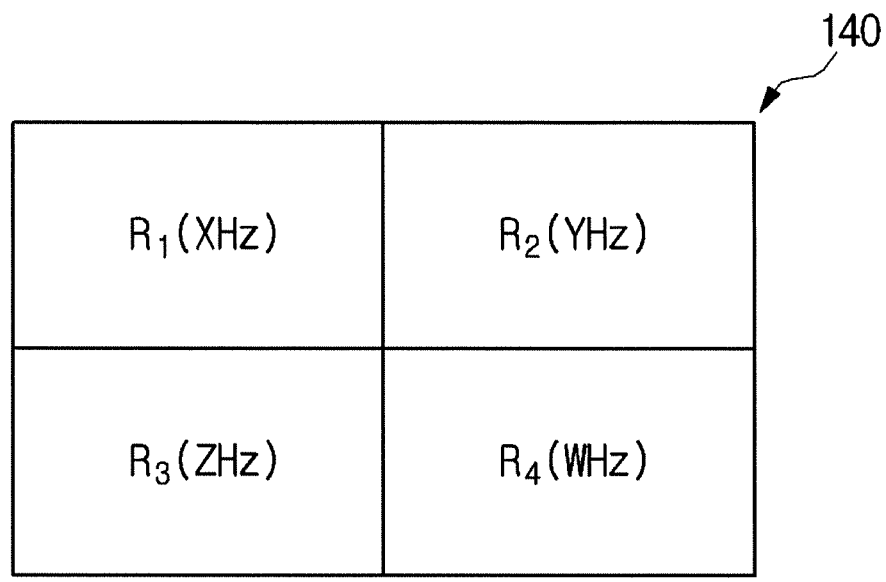
FIG. 7 is a conceptual diagram illustrating an exemplary method for displaying a visual stimulus signal by assigning different frequencies to respective regions of a display unit according to an embodiment of the present invention.

FIG. 7 is a conceptual diagram illustrating an exemplary method for displaying a visual stimulus signal by assigning different frequencies to respective regions of a display unit according to an embodiment of the present invention.

Referring to FIG. 7, the controller 130 may divide a screen image of the display unit 140 into a plurality of regions, and display visual stimulus signals having different frequencies in individual regions. For example, as can be seen from FIG. 7, a screen image of the display unit 140 is divided into four regions ($R_1$, $R_2$, $R_3$, $R_4$). A visual stimulus signal having a frequency of XHz may be displayed on the first region ($R_1$), a visual stimulus signal having a frequency of YHz may be displayed on the second region ($R_2$), a visual stimulus signal having a frequency of ZHz may be displayed on the third region ($R_3$), and a visual stimulus signal having a frequency of WHz may be displayed on the fourth region ($R_4$). In this case, X, Y, Z, and W may be denoted by different frequency values.

Referring to FIG. 7, if several regions contained in one screen image display visual stimulus signals have different frequencies, various user intentions can be recognized using only one screen image.

If the user gazes at the visual stimulus signal displayed on the display unit 140, an EEG signal synchronized with the frequency of the visual stimulus signal is generated, and the EEG signal is detected by the EEG detector 200.

Figure 8:
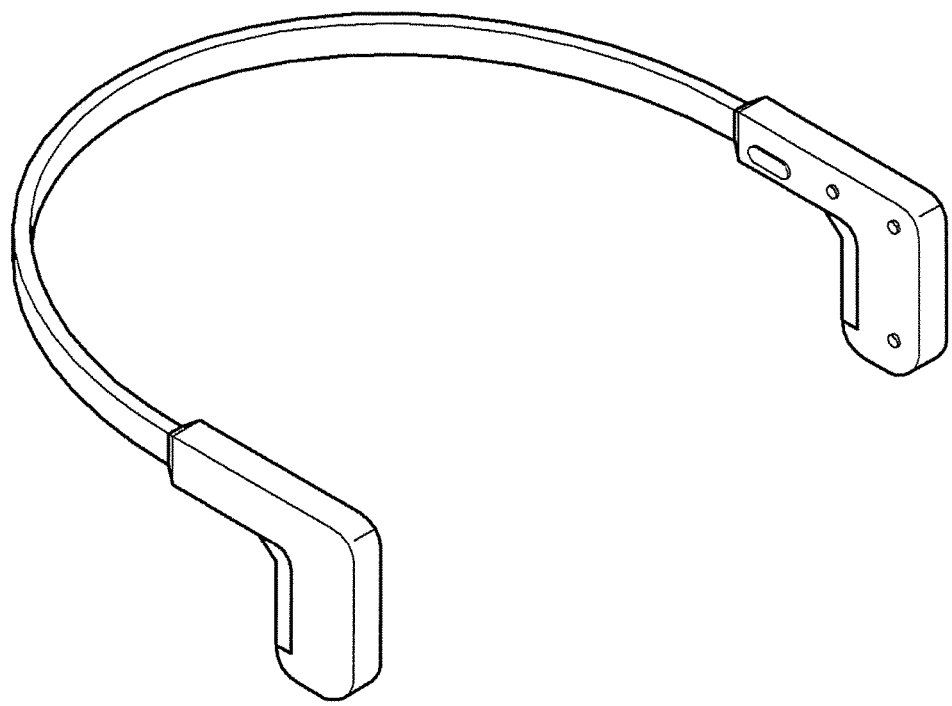
FIG. 8 is a view illustrating an external appearance of an electroencephalogram (EEG) detector according to an embodiment of the present invention.
Figure 9:
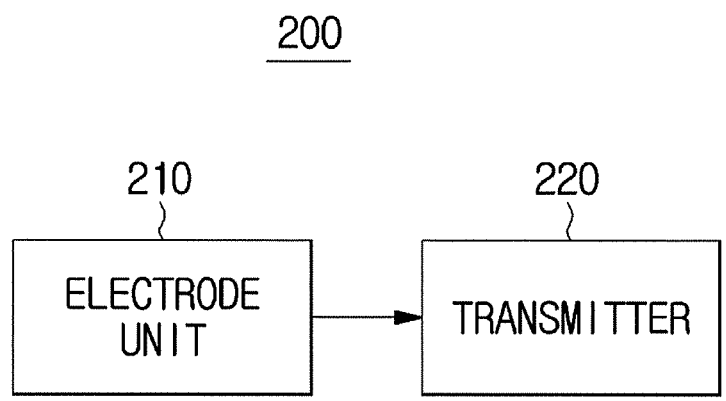
FIG. 9 is a control block diagram illustrating an EEG detector according to an embodiment of the present invention.

FIG. 8 is a view illustrating an external appearance of an electroencephalogram (EEG) detector according to an embodiment of the present invention. FIG. 9 is a control block diagram illustrating an EEG detector according to an embodiment of the present invention.

Referring to FIG. 8, the EEG detector 200 is formed in a wearable manner so that the user can wear the EEG detector 200. The EEG detector 200 worn by the user may be connected to the display apparatus 100 by wire or wirelessly.

Referring to FIG. 9, the EEG detector 200 may include an electrode unit 210 for detecting the EEG signal, and a transmitter for transmitting the signal detected by the electrode unit 210 to the display unit 100.

The electrode unit 210 may include a plurality of EEG measurement electrodes capable of being attached to the scalp, and the plurality of EEG measurement electrodes may be classified into a signal electrode and a reference electrode.

If several EEG measurement electrodes are attached to the occipital lobe, the flow of electricity generated when signals are communicated between cranial nerves in the nervous system may be measured by the EEG measurement electrode.

The transmitter 220 may transmit the EEG signal detected by the electrode unit 210 to the display apparatus 100 by wire or wirelessly. In this case, the transmitted EEG signal may be an analog signal or a digital signal. When transmitting the digital EEG signal, an analog-to-digital converter (ADC) may be contained in the transmitter 220 for converting the detected EEG signal to the digital EEG signal.

If the EEG detector 200 is connected to the display apparatus 100 by wire, the transmitter 200 may include a cable for connecting the EEG detector 200 to the display apparatus 100. In this case, the communication unit 110 of the display apparatus 100 may include a terminal capable of being connected to the cable.

If the EEG detector 200 is wirelessly connected to the display apparatus 100, each of the transmitter 220 and the communication unit 110 may include at least one communication module selected from among a group that includes a Bluetooth communication module, a Bluetooth low energy (BLE) communication module, Ultra Wideband (UWB), ZigBee, a Digital Living Network Alliance (DLNA) module, a near field communication (NFC) module, etc.

However, a communication scheme between the EEG detector 200 and the display apparatus 100 is not limited to the above example, and the EEG detector 200 and the display apparatus 100 can also communicate with each other using other communication schemes other than the above-mentioned examples without departing from the scope or spirit of the present invention.

Meanwhile, the EEG detector 200 may convert the EEG signal detected by the electrode unit 210 into a raw signal, and may transmit the raw EEG signal to the display apparatus 100. If necessary, the EEG detector 200 performs pre-processing (e.g., amplification, filtering, etc.) of the raw signal, and then transmits the pre-processed resultant signal as necessary. In the former case, the display apparatus 100 having received the EEG signal may perform pre-processing. Although the embodiment of the display apparatus 100 includes the former case and the latter case, the following embodiment will exemplarily disclose the former case in which the display apparatus 100 performs pre-processing.

Figure 10:
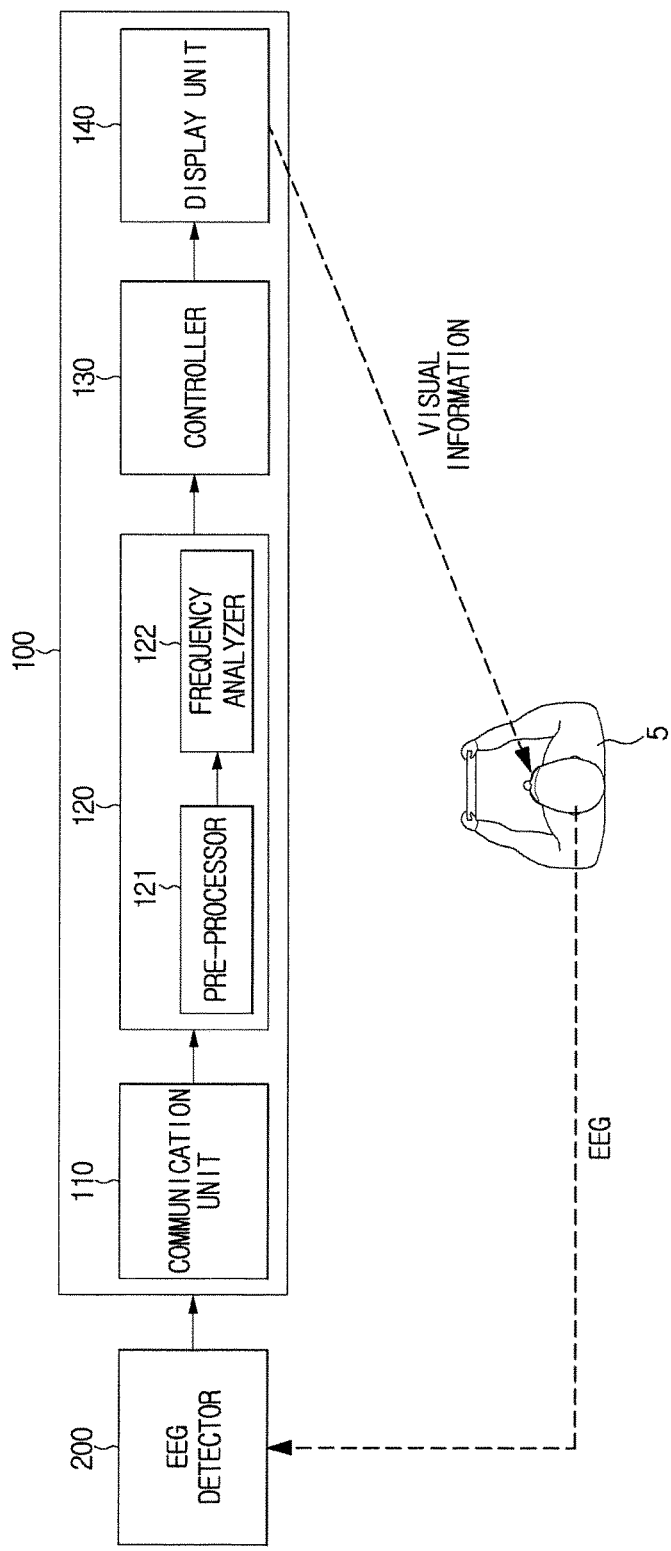
FIG. 10 is a detailed block diagram illustrating an EEG analyzer of a display apparatus according to an embodiment of the present invention.
Figure 11:
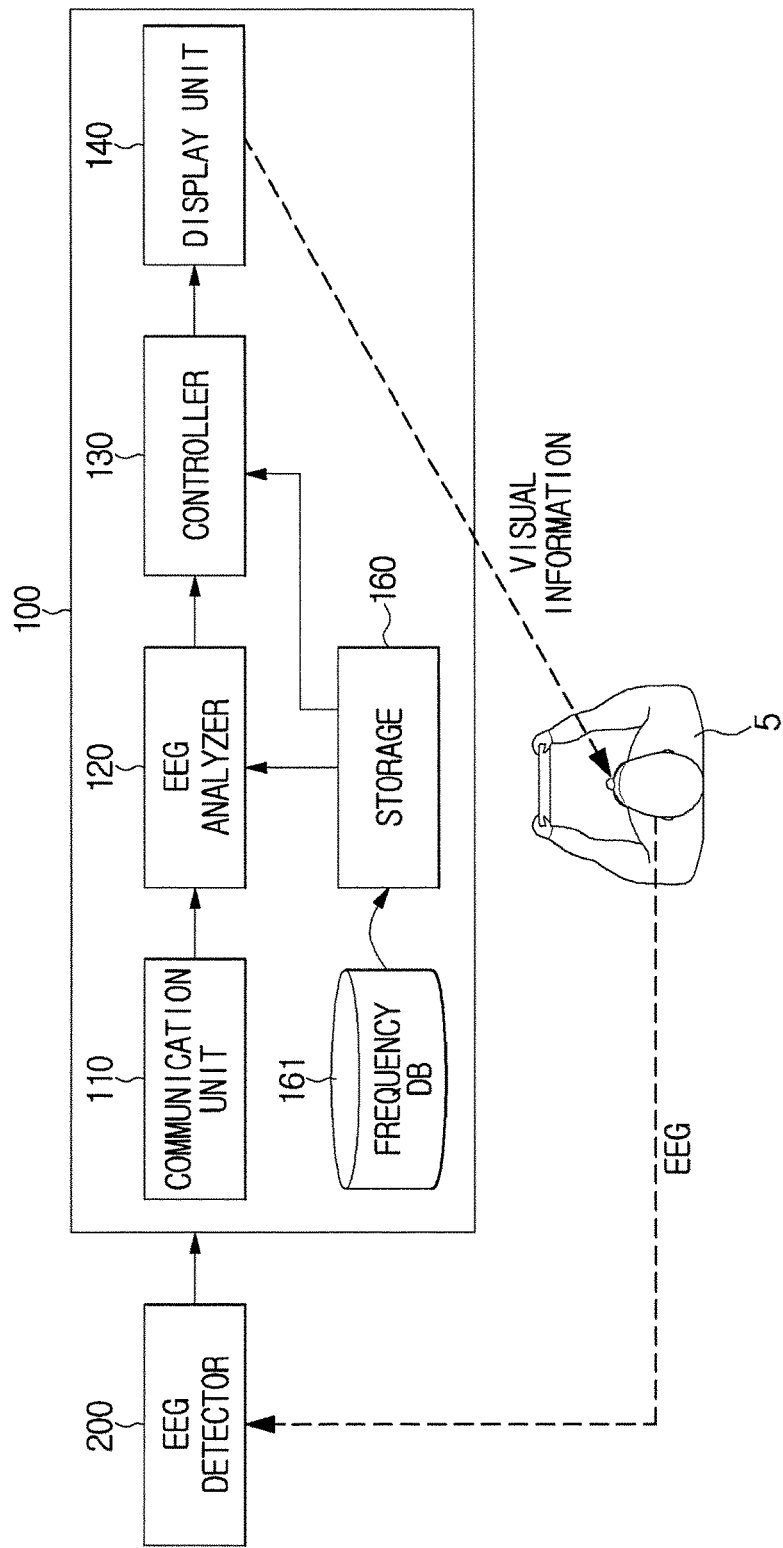
FIG. 11 is a control block diagram illustrating a display apparatus further including a storage, according to an embodiment of the present invention.

FIG. 10 is a detailed block diagram illustrating an EEG analyzer of a display apparatus according to an embodiment of the present invention. FIG. 11 is a control block diagram illustrating a display apparatus further including a storage, according to an embodiment of the present invention.

Referring to FIG. 10, if the communication unit 110 receives the EEG signal of the user from the EEG detector 200, the EEG analyzer 120 may analyze the user EEG signal and recognize the user's eyes. For example, as can be seen from FIG. 10, the EEG analyzer 120 may include a pre-processor 121 for pre-processing the EEG signal, and a frequency analyzer 122 for analyzing the frequency component of the EEG signal.

Although not shown in the drawings, if the EEG signal received from the EEG detector 200 is an analog signal, the communication unit 110 or the EEG analyzer 120 may include an ADC, and the EEG analyzer 120 may analyze the digital EEG signal converted by the ADC.

The EEG signal of the EEG detector 200 may include noise that occurs by signal propagation in the scalp, the twinkling of an eye, movement of facial muscles, a peripheral environment, and basic visual information displayed on the display unit 140. Therefore, the pre-processor 121 may amplify the user EEG signal or may filter noise.

In more detail, only the frequency of a specific region may pass through a frequency band filter such as a high pass filter, or a spatial frequency band may be removed or emphasized by a spatial filter. For example, the frequency signal of less than 0.1 Hz may be cut off using the high pass filter, or a low weight may be allocated to signals generated from a peripheral part of motor cortex using a spatial filter and the EEG signal of the motor cortex to be measured may be amplified.

For example, the spatial filter may be any of a common average reference (CAR) filter, a large surface Laplacian (Large SL) filter, a small surface Laplacian (Small SL) filter, a common spatial pattern (CSP) filter, etc.

Alternatively, noise of the EEG signal may be removed using the noise removal algorithm, for example, an independent component analysis (ICA) algorithm, a linear discriminant analysis (LDA) algorithm, a principal component analysis (PCA) algorithm, a canonical correlation analysis (CCA) algorithm, etc.

The frequency analyzer 122 may analyze the frequency component of the EEG signal. For example, the frequency analyzer 122 may calculate frequency-based power spectrum through Fourier transform, and may search for a specific frequency component by comparing the magnitudes of power spectrum values with each other.

Meanwhile, the EEG signal generated from the user who gazes at the visual stimulus signal may include a fundamental frequency indicating a frequency of the visual stimulus signal and a harmonic frequency indicating a multiple of the fundamental frequency. Therefore, the frequency analyzer 122 may also determine the frequency component of the EEG signal through Cepstrum analysis.

The EEG analyzer 120 may determine whether a specific frequency component is generated during a reference time or more. For example, assuming that the reference time is set to 5 seconds, if a specific frequency component is generated during 5 or more seconds, this means that the user gazes at the corresponding region. Alternatively, this means that the user attempts to execute a function corresponding to the corresponding region gazed at by the user. As a result, a specific function can be prevented from being executed in the case in which the user momentarily gazes at the specific region without any intention.

The construction and detailed operations of the above-mentioned EEG analyzer 120 are merely exemplary, and the scope or spirit of the embodiment of the display apparatus 100 is not limited thereto. Therefore, not only the above-mentioned examples but also other methods or other constructions can be applied to the embodiment of the present invention without departing from the scope or spirit of the present invention so long as the frequency of the EEG signal detected by the EEG detector 200 can be discriminated.

Referring to FIG. 11, the display apparatus 100 may further include a storage 160. A frequency database (DB) 161 of the visual stimulus signal may be stored in the storage 160. A function corresponding to a specific frequency or a region corresponding to the function may be mapped and stored in the frequency DB 161.

The storage 160 may include a Read Access Memory (RAM), a Read Only Memory (ROM), a Hard Disk Drive (HDD), a magnetic disk, an optical disk, a solid static disk, etc.

For example, a radio function may be mapped to the 8 Hz frequency, a Bluetooth function may be mapped to the 10 Hz frequency, a navigation function may be mapped to the 15 Hz frequency, and a telephone function may be mapped to the 12 Hz frequency. In this case, if the user EEG signal detected by the EEG detector 200 includes the 15 Hz frequency, the EEG analyzer 120 can recognize that the user selects a navigation function.

The controller 130 may generate a control signal for controlling the device according to the decision result of the EEG analyzer 120. In this case, if the device to be controlled is an external device, the controller 130 transmits a control signal to an external part. If the display unit 140 is a control target, the controller 130 may re-transmit a control signal to the display unit 140.

The EEG analyzer 120 may include a memory to store a program and data for executing the operations of the above-mentioned constituent elements, and a microprocessor to process data by executing the program stored in the memory. In addition, the respective constituent elements contained in the EEG analyzer 120 may be implemented by an additional microprocessor, and two or more constituent elements of the EEG analyzer 120 may share the microprocessor.

The controller 130 may include a memory to store a program and data for generating a control signal, and a microprocessor to process data by executing the program stored in the memory. In this case, the controller 130 may share a memory or a microprocessor with the EEG analyzer 120, and may also share a memory or a microprocessor with other constituent elements of the display apparatus 100.

In addition, a memory configured to store the program and data of the controller 130 and the EEG analyzer 120 may be included in the storage 160.

The display apparatus 100 according to the embodiment may be contained in a vehicle. A vehicle including the display apparatus 100 according to the embodiment will hereinafter be described in detail.

Figure 12:
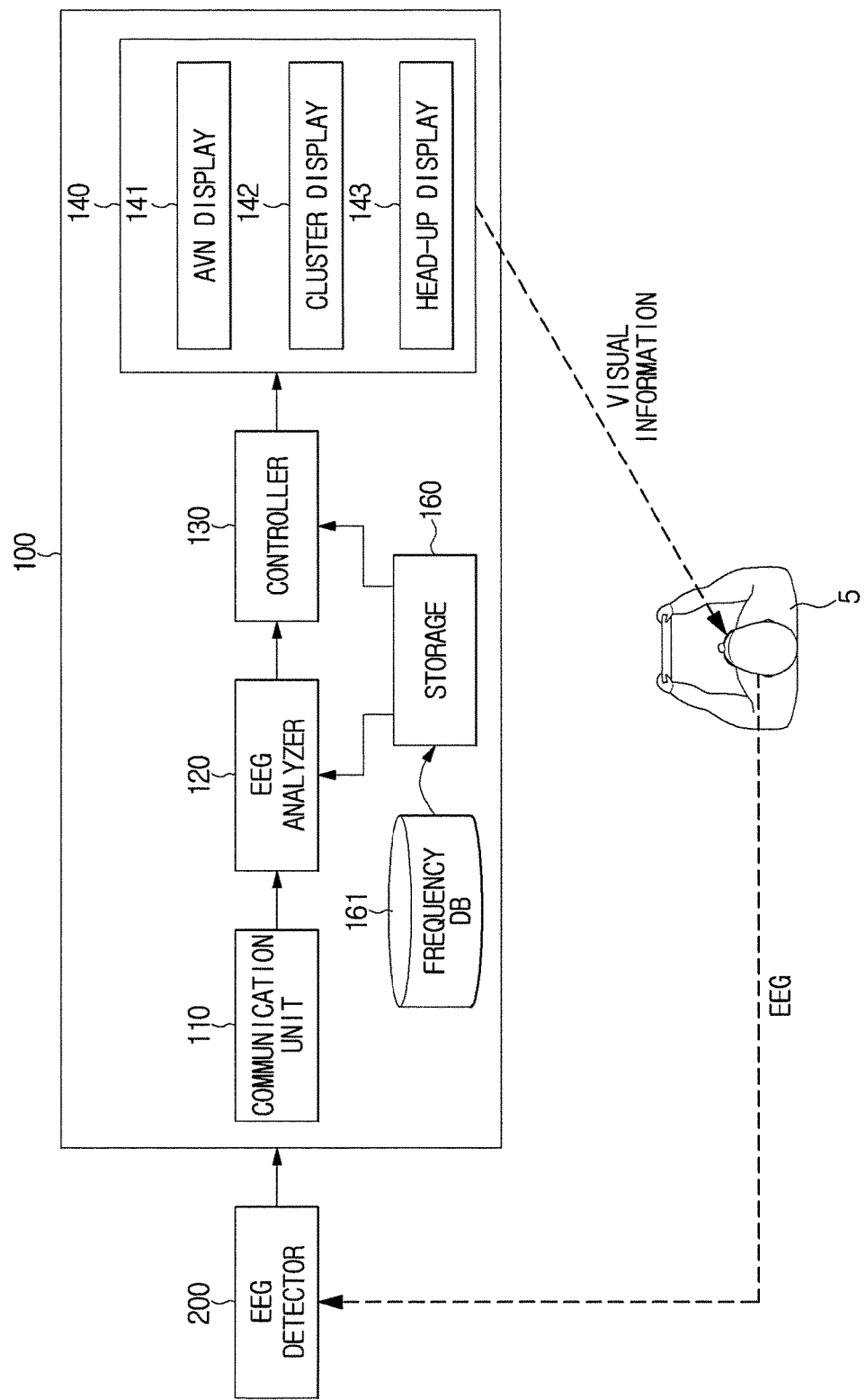
FIG. 12 is a block diagram illustrating a display apparatus contained in a vehicle according to an embodiment of the present invention.
Figure 13:
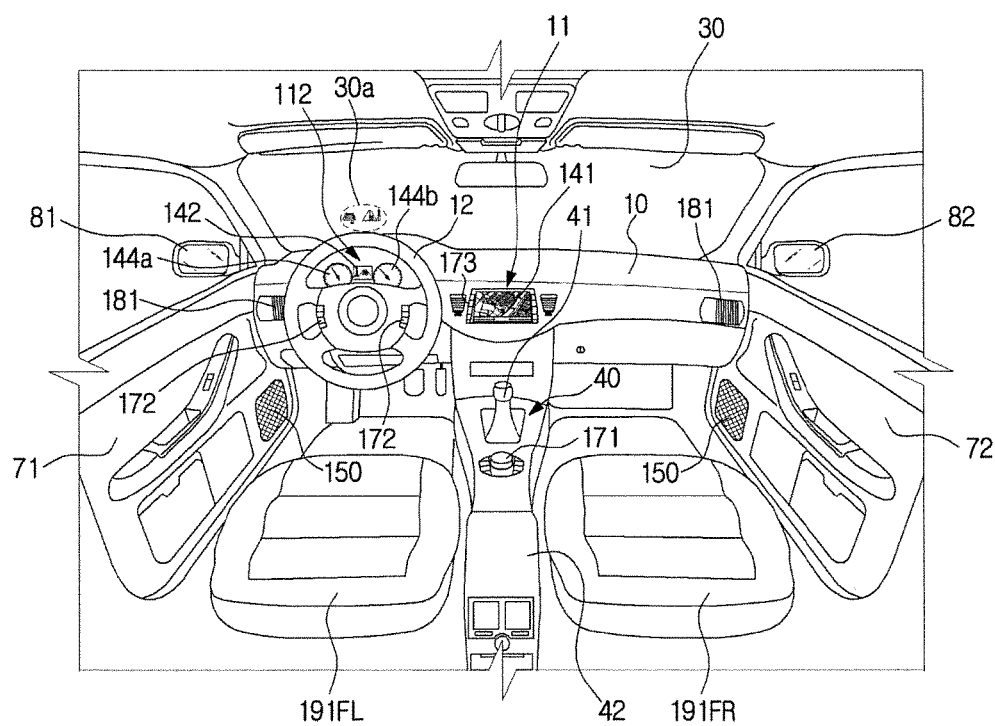
FIG. 13 is a view illustrating an internal structure of a vehicle according to an embodiment of the present invention.
Figure 14:
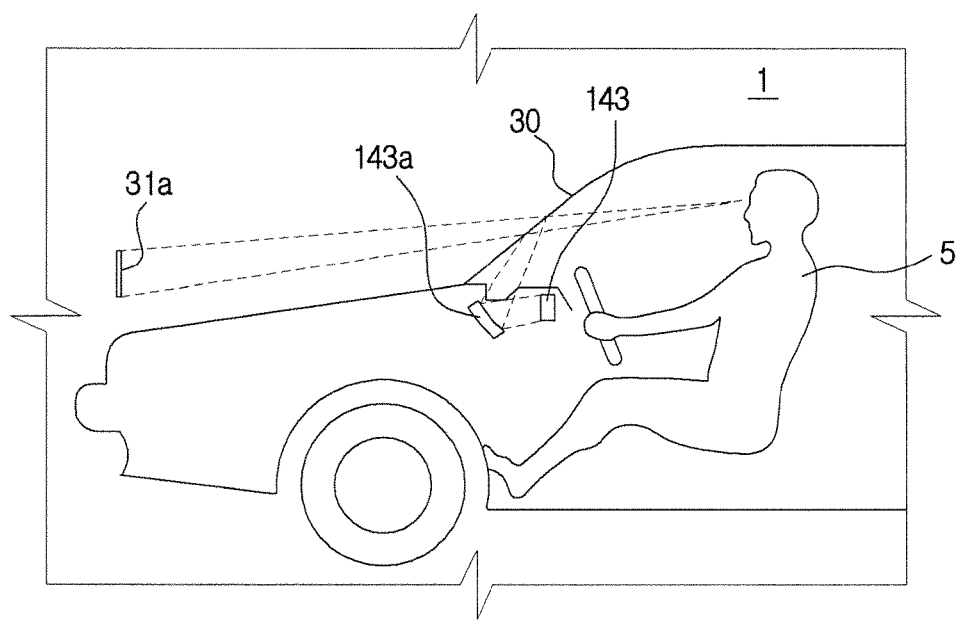
FIG. 14 is a view illustrating a head-up display and associated constituent elements.

FIG. 12 is a block diagram illustrating a display apparatus contained in a vehicle according to an embodiment of the present invention. FIG. 13 is a view illustrating an internal structure of a vehicle according to an embodiment of the present invention. FIG. 14 is a view illustrating a head-up display and associated constituent elements.

If the display apparatus 100 is contained in the vehicle, the display unit 140 for displaying the visual stimulus signal may include an Audio Video Navigation (AVN) display 141, a cluster display 142, and a head-up display 143. Although the display unit 140 of FIG. 12 includes an AVN display 141, a cluster display 142, and a head-up display 143 for convenience of description, it should be noted that the display unit 140 of FIG. 12 may also selectively include one or more of the AVN display 141, the cluster display 142, and the head-up display 143.

As can be seen from FIG. 12, the user may gaze at visual information displayed on at least one of the AVN display 141, the cluster display 142, and the head-up display 143. Although the user who gazes at the visual information does not recognize the visual stimulus signal, the user can also gaze at the visual stimulus signal. If the EEG detector 200 detects the user EEG signal and transmits the detected EEG signal to the display apparatus 100, the EEG analyzer 120 may recognize the user intention by analyzing the EEG signal, and the controller 130 may generate a control signal corresponding to the user intention.

Referring to the internal components of the vehicle 1 shown in FIG. 13, the AVN display 141 may be mounted to a center fascia 11 of a dashboard 10 in such a manner that a user (specifically, a vehicle driver) views or manipulates the displayed image while driving. The center fascia 11 may indicate the center region of the dashboard 10 including a control panel board disposed between a driver seat 191 FL and a passenger seat 191 FR.

The AVN display 141 may be implemented by any one of a Liquid Crystal Display (LCD), a Light Emitting Diode (LED), a Plasma Display Panel (PDP), an Organic Light Emitting Diode (OLED), a Cathode Ray Tube (CRT), etc.

The center fascia 11 may include not only the AVN display 141 but also a ventilation opening 181 through which warm air or cool air generated from an air-conditioning device 180 (shown in FIG. 28) is discharged.

The vehicle may include a tray 42 disposed between the driver seat 191 FL and the passenger seat 191 FR so as to store articles, and a center console 40 including a gear stick 41. An AVN input unit 171 may be contained in the center console 40. For example, the AVN input unit 171 may be implemented by a jog-shuttle or a joystick. If the AVN input unit 171 is implemented by the jog-shuttle, the user may control the AVN function by moving the jog-shuttle forward or backward and to the left or right or by pressing or turning the jog-shuttle. However, the jog-shuttle shown in FIG. 13 is merely an example capable of being applied to the embodiment of the vehicle 1, and the AVN input unit 171 may also be implemented by a hard key, instead of the jog-shuttle or joystick.

Meanwhile, an auxiliary input unit 173 shaped as a hard key may be mounted to a region adjacent to the AVN display 141. Alternatively, if the AVN display 141 is implemented by a touchscreen, an auxiliary input unit 173 shaped as a soft key may also be mounted to one region of the AVN display 141.

A cluster 112 may be provided to a region facing a steering wheel 12 from among the regions of the dashboard 10 in such a manner that a driver who currently drives the vehicle can recognize information displayed on an instrument panel. A cluster display 142 may be implemented by any one of a Liquid Crystal Display (LCD), a Light Emitting Diode (LED), a Plasma Display Panel (PDP), an Organic Light Emitting Diode (OLED), a Cathode Ray Tube (CRT), etc.

The cluster 112 may further include a cluster display 142, a speed gauge 144a for indicating a vehicle speed, and an RPM gauge 144b for indicating a vehicle RPM. The cluster display 142 may be disposed between the speed gauge 144a and the RPM gauge 144b as shown in FIG. 13. However, the scope or spirit of the present invention is not limited thereto, and a detailed position of the cluster display 142 according to the embodiment is not limited.

The cluster input unit 172 formed in a hard key shape is mounted to one region of the steering wheel 12, so that a vehicle driver who grasps the steering wheel 12 can manipulate the cluster input unit 172. Alternatively, the cluster input unit 172 formed in a lever shape is mounted to the rear side of the steering wheel 12, such that the user pushes, or pulls the lever-shaped cluster input unit 172, or moves the lever-shaped cluster input unit 172 up or down so as to control the cluster 112.

The head-up display 143 may not directly provide the user with visual information, and may reflect the visual information and display the reflected visual information on a windshield 30 of the vehicle 1. Referring to FIG. 14, an output image of the head-up display 143 is displayed on one region 30a of the windshield 30, and the head-up display and associated constructions will hereinafter be described with reference to FIG. 14.

Referring to FIG. 14, the head-up display 143 may be provided at the front of the vehicle 1, and a reflection plate 143a may be provided at the front of the head-up display 143. If the head-up display 143 outputs an image in a forward direction, the output image is reflected from the reflection plate 143a and projected onto the windshield 30. In this case, the windshield 30 may operate as a combiner.

The projected image is reflected from the windshield 30 and transmitted to the eyes of the user 5. Although the user 5 views the image displayed on the display region 30a of the windshield 30 as shown in FIG. 5, the image viewed by the user's eyes is a virtual image 31 a formed at the outside of the windshield 30.

The head-up display 143 shown in FIG. 14 and associated constructions are merely exemplary, the head-up display 143 may include a plurality of reflection plates 143a, may not include the reflection plates 143a, or may additionally include a diffraction element.

An input unit for manipulating the head-up display 143 may also be separately included. The cluster input unit 172 mounted to the steering wheel 12 may also function as the input unit for manipulating the head-up display 143.

Alternatively, one of the cluster input units 172 respectively provided at the left side and the right side of the steering wheel 12 may operate as the input unit for manipulating the cluster display 142, and the other one may also function as the input unit for manipulating the head-up display 143.

Alternatively, each cluster input unit 172 formed in a lever shape is mounted to the rear side of the steering wheel 12, such that the user pushes, or pulls the lever-shaped cluster input unit 172, or moves the lever-shaped cluster input unit 172 up or down so as to control the head-up display 143.

In contrast, although FIG. 13 has exemplarily disclosed the input unit for controlling the AVN display 141, the input unit for controlling the cluster display, and the input unit for controlling the head-up display for convenience of description, only some of the above-mentioned input units are used, such that only one input unit may receive a command for controlling a plurality of display units. For example, the AVN input unit 171 may receive not only a command for controlling the AVN display but also a command for controlling the cluster display 142 or the head-up display 143.

Figure 15:
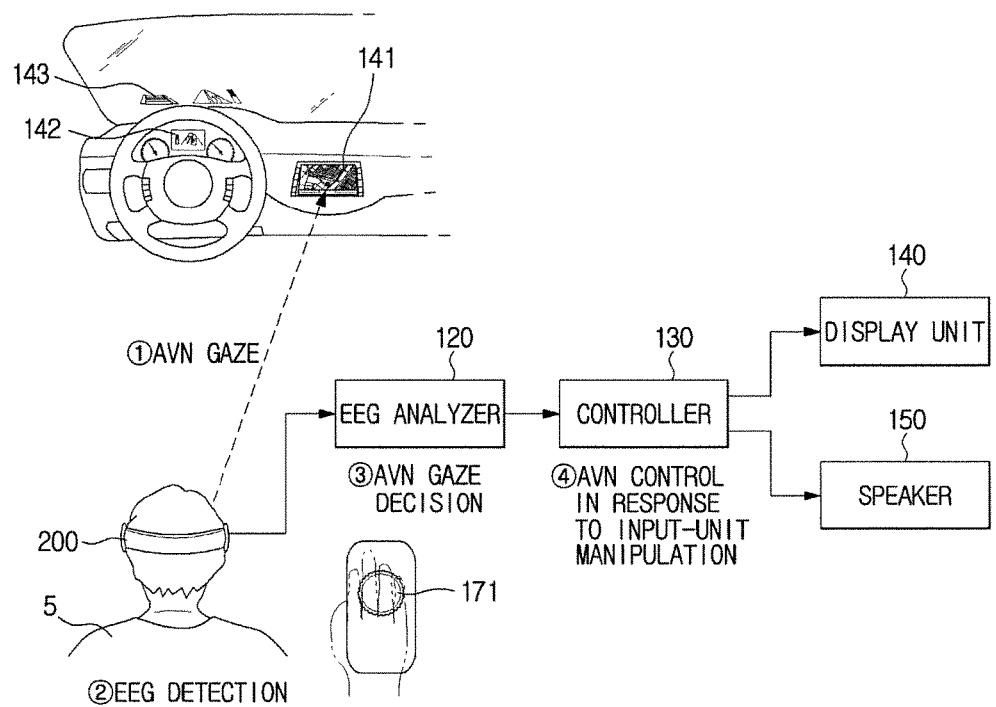
FIG. 15 is a conceptual diagram illustrating an exemplary control operation according to user-gazed regions.

FIG. 15 is a conceptual diagram illustrating an exemplary control operation according to user-gazed regions.

As described above, the display apparatus 100 determines the user-gazed region by analyzing the user EEG signal, and controls the device corresponding to the user-gazed region. For example, if the user 5 gazes at any one of the AVN display 141, the cluster display 142, and the head-up display 143, the user 5 can display the user-gazed display by manipulating the input unit provided in the vehicle 1. For this purpose, the visual stimulus signals having different frequencies may be respectively inserted into visual information displayed on the AVN display 141, the cluster display 142, and the head-up display 143.

FIG. 15 illustrates an exemplary case in which the user 5 gazes at the AVN display 141. Referring to FIG. 15, if the user gazes at the AVN display 141, the EEG signal having the frequency of a visual stimulus signal displayed on the AVN display may occur in the occipital lobe of the user 5. If the EEG detector 200 detects the EEG signal of the user 5, the EEG analyzer 120 may determine the frequency by analyzing the detected EEG signal. If the frequency of the EEG signal is a frequency corresponding to the AVN display 141 (i.e., if the frequency of the EEG signal is a frequency of a visual stimulus signal displayed on the AVN display 141), this means that the user currently gazes at the AVN display 141. In this case, associated information is mapped to a display region of the visual stimulus signal having a specific frequency and to a display region of the visual stimulus signal having the corresponding frequency, such that the stored frequency database (DB) may be used.

If the user 5 gazes at the AVN display 141, this means that the AVN function can be controlled using the input unit. Therefore, although the user 5 manipulates a certain input unit, the controller 130 can control the AVN function according to this manipulation, and the controller 130 may also control the display unit 140 or the speaker 150 so as to output content corresponding to the corresponding function. Although FIG. 15 illustrates that the user 5 manipulates the AVN input unit 171, the AVN function may also be controlled by manipulation of the cluster input unit 172. Although the user 5 gazes at the cluster display 142 or the head-up display region 30a, the cluster display 142 or the head-up display 143 may also be controlled by manipulation of the AVN input unit 171.

Meanwhile, FIG. 7 has exemplarily disclosed that one screen is divided into a plurality of regions and different frequencies are allocated to the plurality of regions. Therefore, the AVN display 141, the cluster display 142, or the head-up display 143 is divided into a plurality of regions, and different control methods may be used according to which region is gazed at by the user. A detailed description thereof will hereinafter be given with reference to FIGS. 16 and 17.

Figure 16:
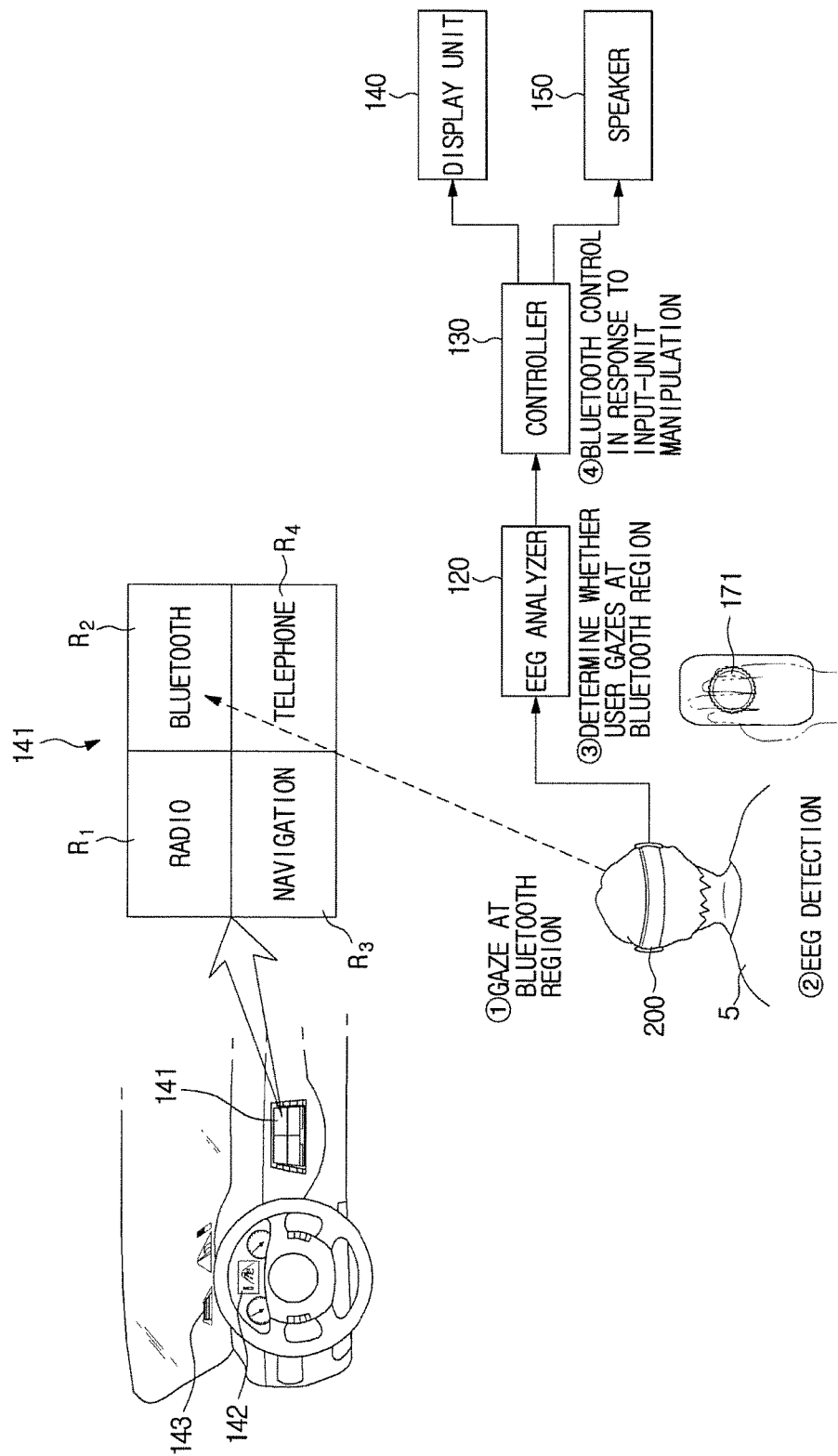
FIG. 16 is a conceptual diagram illustrating an exemplary method for dividing one display into a plurality of regions and allocating different frequencies to the divided regions.
Figure 17:
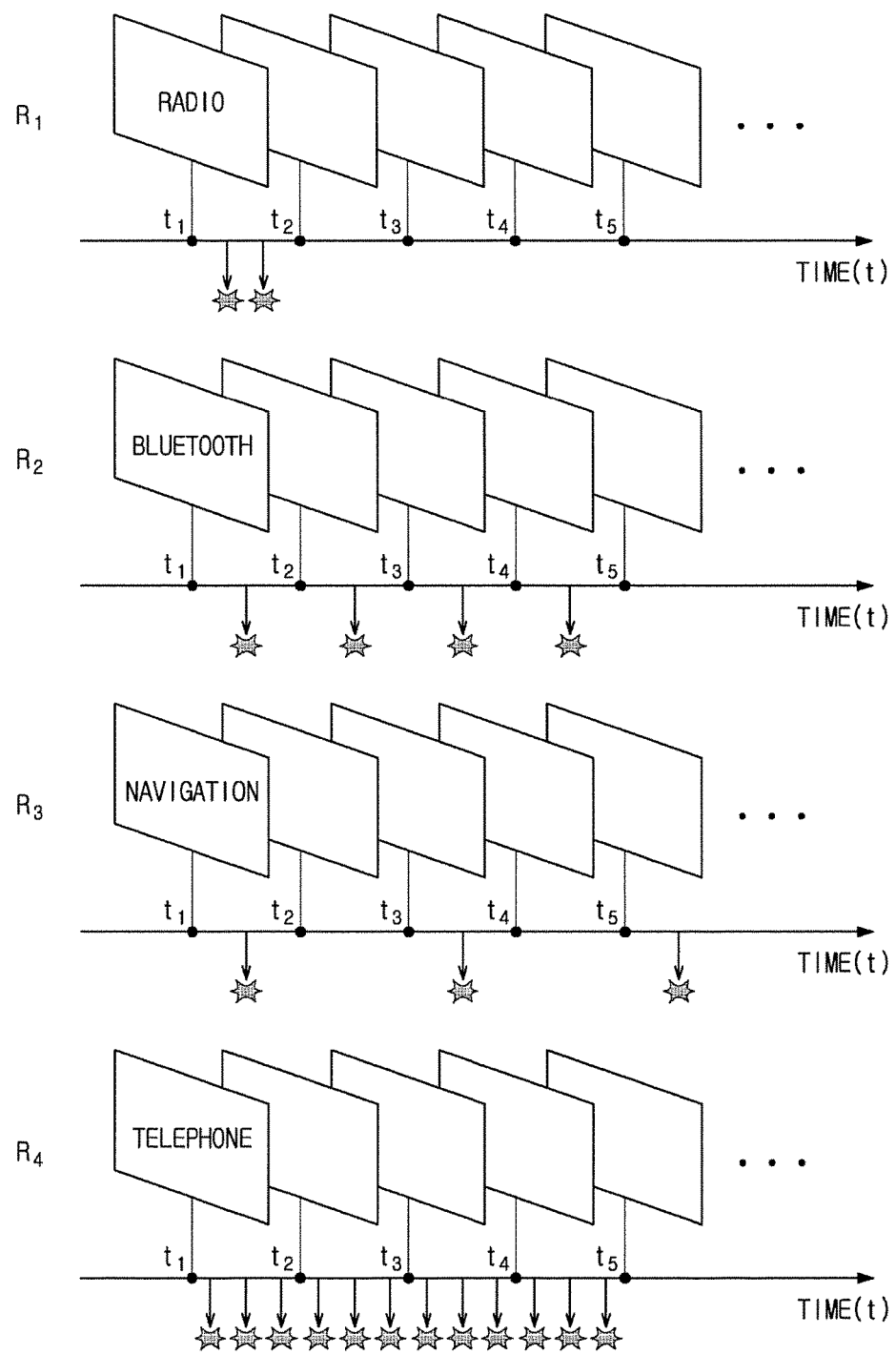
FIG. 17 is a conceptual diagram illustrating an exemplary method for displaying visual stimulus signals having different frequencies on the divided regions.

FIG. 16 is a conceptual diagram illustrating an exemplary method for dividing one display into a plurality of regions and allocating different frequencies to the regions. FIG. 17 is a conceptual diagram illustrating an exemplary method for displaying visual stimulus signals having different frequencies on the divided regions.

Referring to FIG. 16, the AVN display 141 is divided into four regions ($R_1$, $R_2$, $R_3$, $R_4$), a radio function may be allocated to the first region ($R_1$), a Bluetooth function may be allocated to the second region ($R_2$), a navigation function may be allocated to the third region ($R_3$), and a telephone function may be allocated to the fourth region ($R_4$).

In order to determine which one of four regions is gazed at by the user 5, the visual stimulus signals having different frequencies may be displayed on four regions. Referring to FIG. 17, if the user gazes at the radio region ($R_1$), visual information indicating selection of the radio function may be displayed on the radio region ($R_1$), and a visual stimulus signal may be inserted between frames constructing the visual information. Two visual stimulus signals are inserted into two successive frames so as to generate the frequency.

If the user gazes at the Bluetooth region ($R_2$), visual information indicating selection of the Bluetooth function may be displayed on the Bluetooth region ($R_2$), and a visual stimulus signal may be inserted between frames constructing the visual information. One visual stimulus signal is inserted between two successive frames, such that a frequency different from the frequency of the visual stimulus signal displayed on the radio region ($R_1$) may be generated.

If the user gazes at the navigation region ($R_3$), visual information indicating selection of the navigation function may be displayed on the navigation region ($R_3$), and the visual stimulus signal may be inserted between frames constructing the visual information. One visual stimulus signal may be alternately inserted between two successive frames, such that a frequency different from those of visual stimulus signals displayed on the radio region ($R_1$) and the Bluetooth region ($R_2$) may be generated.

If the user gazes at the telephone region ($R_4$), visual information indicating selection of the telephone function may be displayed on the telephone region ($R_4$), and the visual stimulus signal may be inserted between frames constructing the visual information. Three visual stimulus signals may be inserted between two successive frames, such that a frequency different from those of the visual stimulus signals displayed on the radio region ($R_1$), the Bluetooth region ($R_2$), and the navigation region ($R_3$) may be generated.

Referring to FIG. 16, if the user 5 gazes at the Bluetooth region ($R_2$), the EEG signal having the frequency allocated to the Bluetooth region ($R_2$) may occur in the occipital lobe, and the EEG detector 200 may detect this EEG signal. The EEG analyzer 120 analyzes the detected EEG signal, such that it is determined that the user 5 currently gazes at the Bluetooth region.

If the user 5 gazes at the Bluetooth region, this means that the user 5 desires to control the Bluetooth function by manipulating the input unit. Therefore, although the user 5 manipulates a certain input unit, the controller 130 may control the Bluetooth function according to this manipulation, and may control the display unit 140 or the speaker 150 so as to output content corresponding to the Bluetooth function.

Although FIG. 16 has exemplarily disclosed that the user 5 manipulates the AVN input unit 171, it should be noted that the Bluetooth function may also be controlled by manipulation of the cluster input unit 172.

Meanwhile, only some regions from among the screen images of the display unit 140 may also be used to recognize the user's eyes. In addition, if the user gazes at a specific region, this means that the function corresponding to the corresponding region can be controlled by manipulation of the input unit. However, the operation of the user who gazes at a specific region may also be used as an input action of the control command. A detailed description thereof will hereinafter be given with reference to FIGS. 18 and 19.

Figure 18:
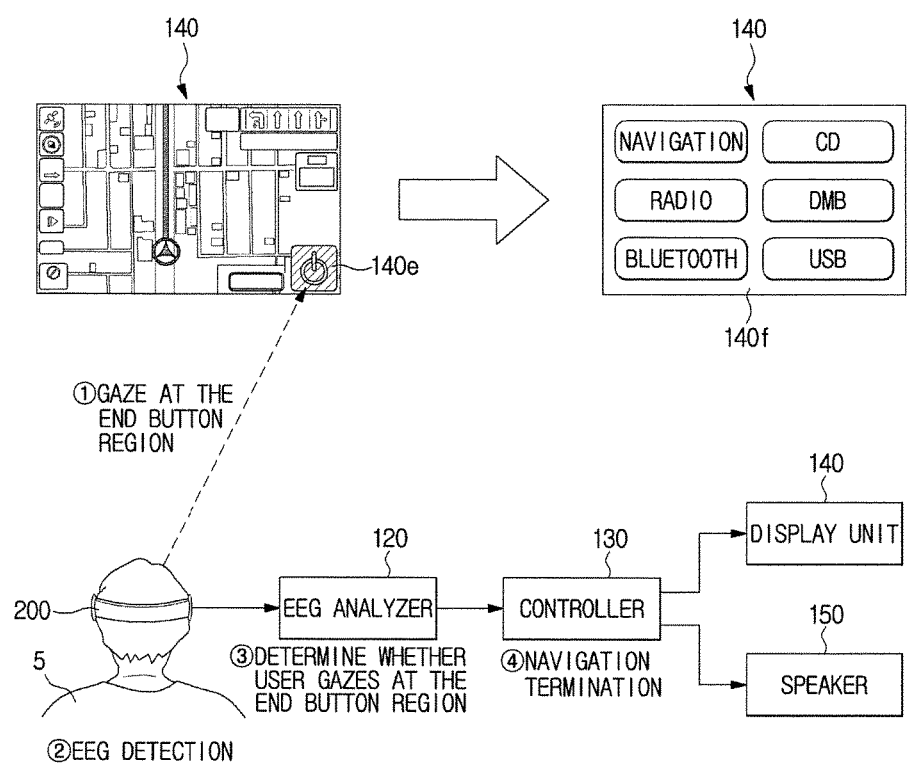
FIGS. 18 and 19 are conceptual diagrams illustrating other control operations according to user-gazed regions.
Figure 19:
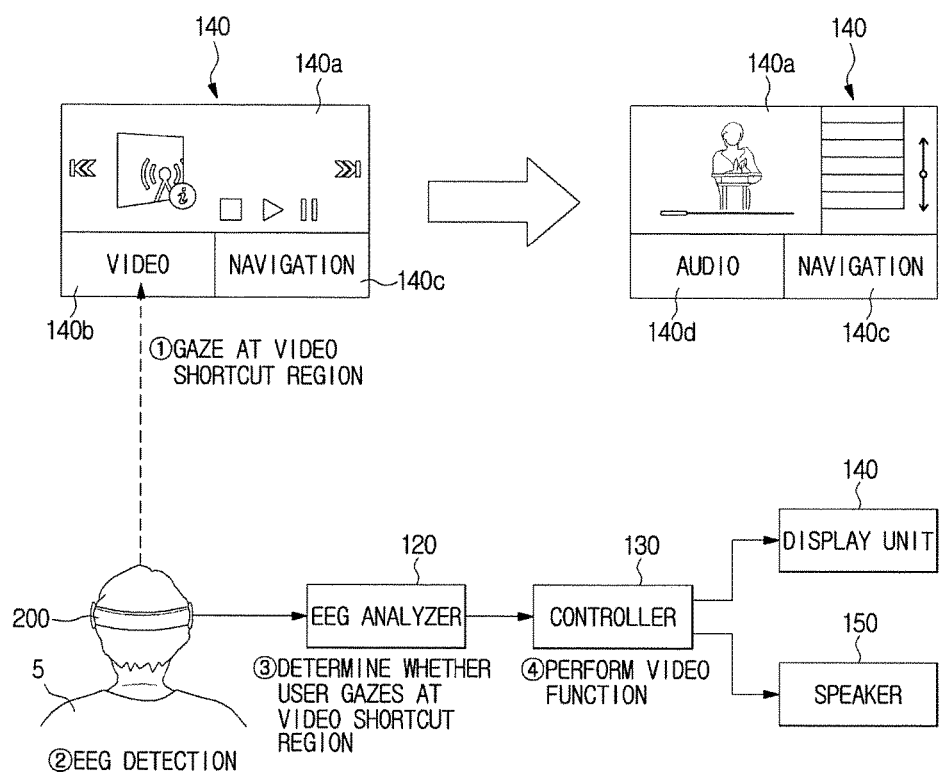

FIGS. 18 and 19 are conceptual diagrams illustrating other control operations according to user-gazed regions.

Referring to FIG. 18, a main screen image 140a associated with the currently executed function may be displayed on the display unit 140. For example, the main screen image 140a may be a navigation screen image. The end button region 140e may be displayed on one region of the display unit 140. If the user gazes at the end button region 140e, visual information indicating that the currently executed function can be terminated may be displayed on the end button region 140e, and a visual stimulus signal having a specific frequency may be inserted between frames constructing the visual information. Information regarding the specific frequency may be stored in the storage 160.

If the user 5 gazes at the end button region 140e, the EEG signal having the frequency of the visual stimulus signal displayed on the end button region 140e may occur in the occipital lobe, and the EEG detector 200 may detect the EEG signal. The EEG analyzer 120 analyzes the detected EEG signal, such that the EEG analyzer 120 can determine that the user 5 gazes at the end button region 140e.

If the user 5 gazes at the end button region 140e, this means that the user desires to terminate the navigation function. Therefore, the controller 130 may immediately terminate the navigation function, and the initial menu screen image 140f instead of the navigation screen image 140a may be displayed on the display unit 140.

As can be seen from FIG. 19, a plurality of shortcut regions at which the corresponding function can be immediately performed according to recognition of the user's eyes may be displayed according to individual functions. In this case, the shortcut region may indicate that the corresponding function is immediately performed without additional manipulation. Referring to FIG. 19, the main screen image 140a associated with the currently executed function may be displayed on some parts of the display unit 140, and the video shortcut region 140b and the navigation shortcut region 140c may be displayed on the other parts of the display unit 140.

The controller 130 may display the visual stimulus signals having different frequencies on the video shortcut region 140b and the navigation shortcut region 140c. In this case, the basic visual information associated with the currently executed function may be displayed on the main screen image 140a, and the visual stimulus signal for recognition of the user's eyes may not be displayed thereon.

If the user gazes at the video shortcut region 140b, basic visual information indicating that the video shortcut function can be executed may be displayed on the video shortcut region 140b, and the visual stimulus signal may be inserted between the frames constructing the basic visual information. If the user gazes at the navigation shortcut region 140c, basic visual information indicating that the navigation shortcut function can be executed may be displayed on the navigation shortcut region 140c, and the visual stimulus signal may be inserted between the frames constructing the basic visual information.

If the user 5 gazes at the video shortcut region 140b, the EEG signal having the frequency of the visual stimulus signal displayed on the video shortcut region 140b may occur in the occipital lobe of the user 5, and the EEG detector 200 may detect the EEG signal. The EEG analyzer 120 analyzes the detected EEG signal, so that the EEG analyzer 120 can determine that the user 5 currently gazes at the video shortcut region 140b.

If the user 5 gazes at the video shortcut region 140b, this means that the user 5 desires to execute the video function. Accordingly, the controller 130 may immediately execute the video function. Simultaneously, the main screen image 140a of the display unit 140 may be switched to the video screen image, and the audio shortcut region 140d instead of the video shortcut region may be displayed.

Although FIG. 19 has exemplarily disclosed the video shortcut region and the navigation shortcut region for convenience of description, the scope or spirit of the present invention is not limited thereto, and there is no limitation in category and number of shortcut functions. In addition, the number and category may be adaptively established according to the use history of the user. For example, the storage 160 may store specific information indicating which function is frequently selected by the user, or may store specific information indicating which function is frequently used. In addition, the function frequently selected or used by the user may be set to the shortcut function. This shortcut function may be periodically updated according to the accumulated use history information. The use history information may be obtained on the basis of the input control command information received from the input unit or the EEG analysis result.

In addition, even when one screen is divided into a plurality of regions as shown in FIG. 16, the size of each region can be adaptively adjusted according to the use history information of the user. A detailed description thereof will hereinafter be given with reference to FIG. 20.

Figure 20:
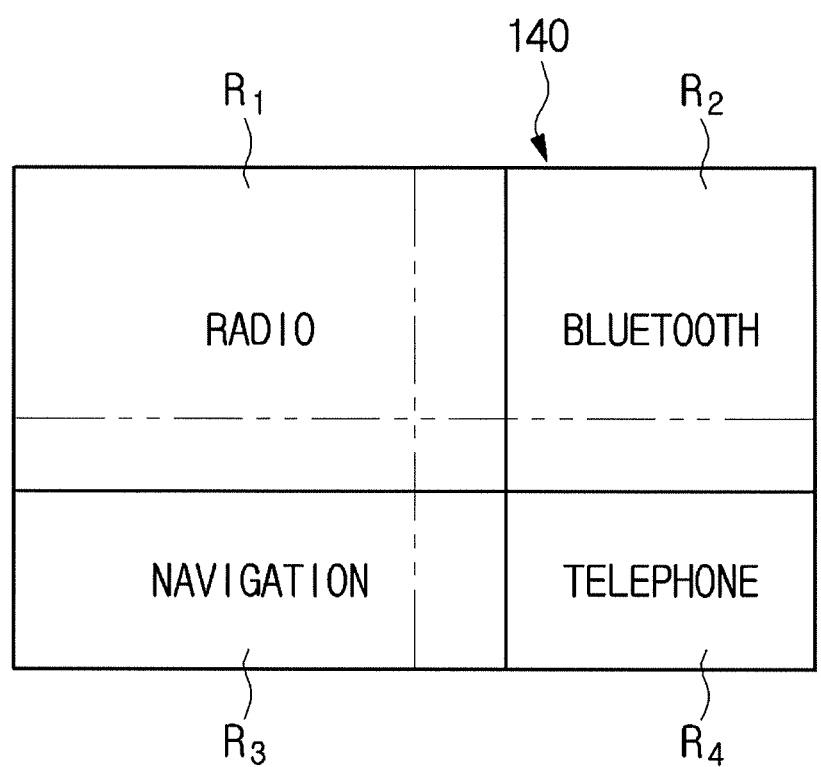
FIG. 20 is a conceptual diagram illustrating an exemplary method for adjusting the sizes of plural regions when a screen image of a display unit is divided into the plural regions.

FIG. 20 is a conceptual diagram illustrating an exemplary method for adjusting the sizes of plural regions when a screen image of a display unit is divided into the plural regions.

Referring to FIG. 20, when one screen image of the display unit 140 is divided into a plurality of regions and the visual stimulus signals having different frequencies are displayed on the respective regions, the region corresponding to the function frequently selected by the user may be enlarged in size such that the enlarged region can be displayed.

For example, if the user frequently selects the radio function, the radio region ($R_1$) can be enlarged in size as shown in FIG. 20. In addition, the remaining regions may be adjusted in size according to the order of frequencies selected by the user.

In addition, the positions of respective regions may also be adjusted according to the order of user-selected frequencies as necessary. For example, the region corresponding to the frequently selected function may be arranged above the screen or arranged at the center part of the screen.

Figure 21:
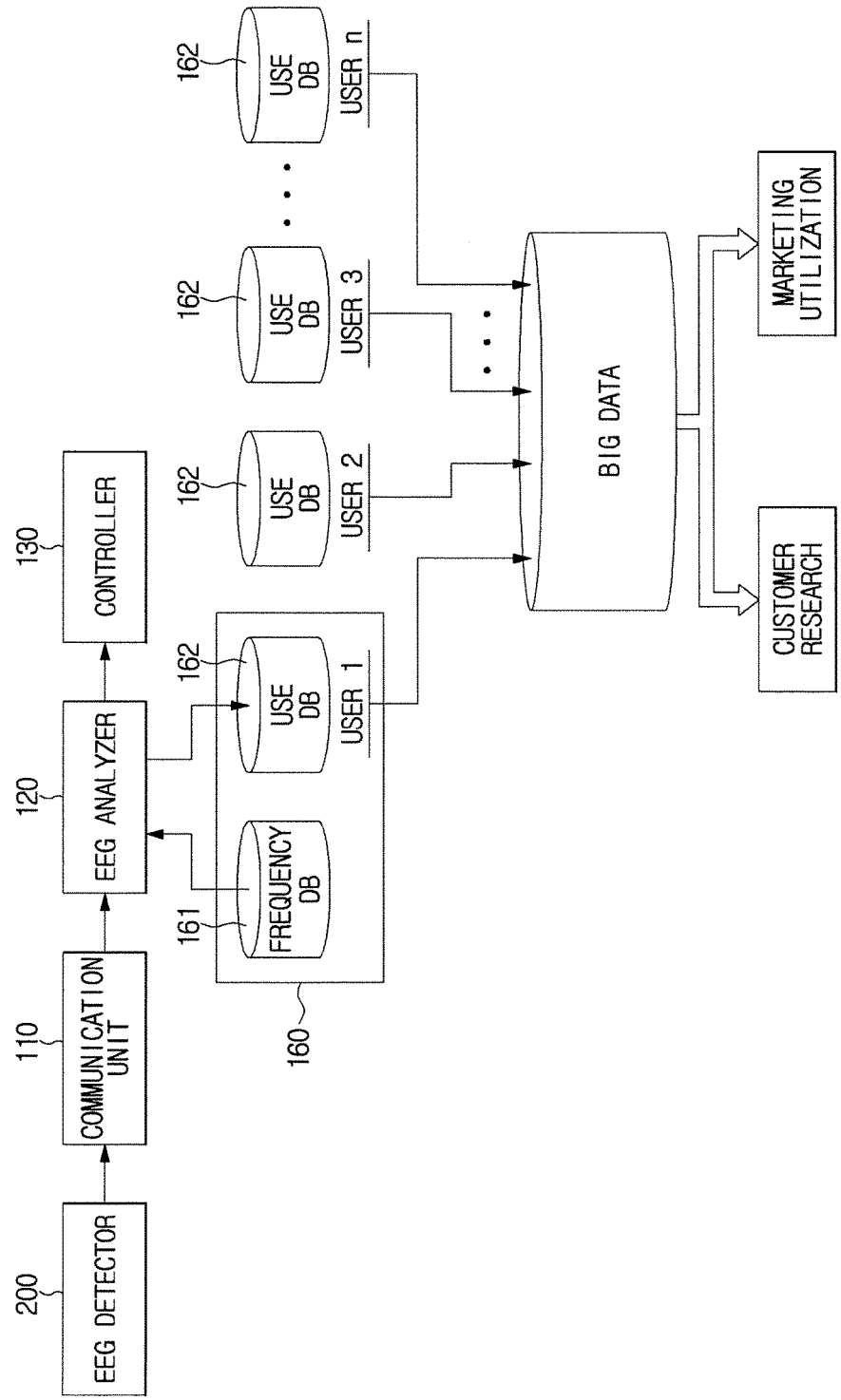
FIG. 21 illustrates various utilization fields of use history information of a user.

FIG. 21 illustrates various utilization fields of use history information of a user.

Referring to FIG. 21, the above-mentioned use history information of the user may be stored in the form of a database (DB), and this DB will hereinafter be referred to as a use database (DB) 162. Only the use history information decided by recognition of the user's eyes may be stored in the use DB 162, the use history decided on the basis of the manipulation of the input unit may also be stored in the use DB 162, and the use history decided by execution history of each function may also be stored in the use DB 162.

The use history information may be used to display the above-mentioned user-adaptive screen image within one vehicle 1. If use history information is collected from a plurality of vehicles used by a plurality of users, the collected history information may be used as big data utilized for customer research or marketing research.

Through the customer search based on big data, it can be recognized which function of the vehicle is preferred by the user, so that a new vehicle can be developed on the basis of the recognized result. For example, when several users execute a specific function, if it is determined that a control command is frequently input through recognition of the user's eyes instead of through manipulation of the input unit, such preference is reflected in a user interface mounted to the vehicle, and the user interface can be customized.

In addition, marketing for vehicle sales on the basis of user-preferred functions may also be performed.

Figure 22:
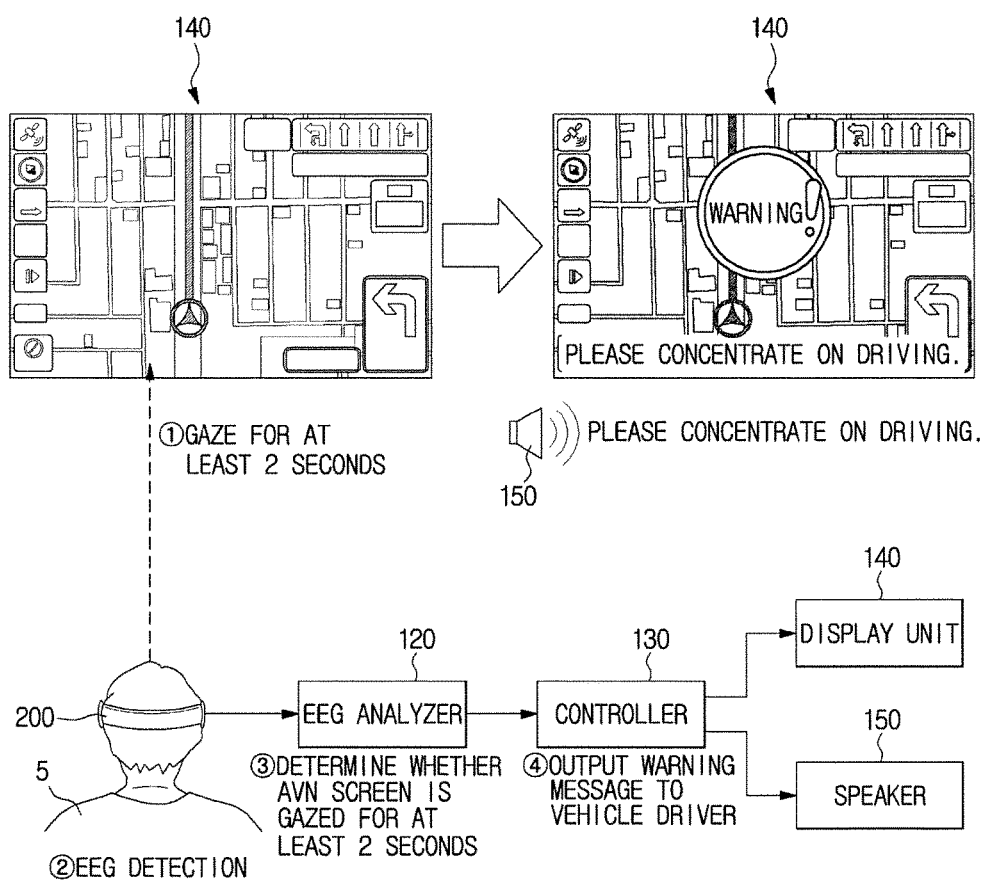
FIG. 22 is a conceptual diagram illustrating another example of a control operation according to user-gazed regions.

FIG. 22 is a conceptual diagram illustrating another example of a control operation according to user-gazed regions.

Although the above-mentioned examples have disclosed that a specific operation of the user who gazes at a specific region indicates that the user desires to execute a specific function corresponding to the user-gazed region, if the user acting as a vehicle driver gazes at the display unit 140 for a long time, the above-mentioned user operation may prevent safe driving.

Referring to FIG. 22, if the user 5 gazes at the display unit 140, the EEG signal having the frequency of a visual stimulus signal displayed on the display unit 140 may occur in the occipital lobe. If the EEG detector 200 detects the EEG signal of the user 5, the EEG analyzer 120 analyzes the detected EEG signal, such that it is determined whether the detected EEG signal has the frequency of the visual stimulus signal, and it is also determined whether the EEG signal having the corresponding frequency is generated during a predetermined reference time or more. In the above-mentioned example, the predetermined reference time is set to 2 seconds.

If the analysis result indicates that the user 5 gazes at the AVN display 141 for 2 or more seconds, the controller 130 may inform a vehicle driver of a warning message through the display 141 or the speaker 150. For example, the warning message for commanding the vehicle driver to concentrate on driving may be displayed in a text form on the AVN display 141, or the warning message may be output audibly through the speaker 150. If necessary, the sound-type warning message may be output alone or may be output simultaneously with the text-type warning message.

Although FIG. 22 exemplarily illustrates that the user gazes at the AVN display 141, even when the user gazes at the cluster display 142 or the head-up display region 30a for a predetermined reference time or more, the warning message may be displayed. In this case, when the user gazes at the cluster display 142, the warning message may also be displayed on the cluster display 142. When the user gazes at the head-up display 143, the warning message may also be displayed on the head-up display 143.

The reference time may be established through experimentation, statistical analysis, or simulation. Several display units (141,142,143) mounted to the vehicle 1 are installed at different positions. When the user gazes at the respective display units (141,142,143), the user's driving state is differently affected according to which one of the display units (141,142,143) is gazed at by the user, such that different reference times may be assigned to individual display units (141,142,143). For example, the shortest reference time may be assigned to the AVN display 141 located farthest from the user's view, and the longest reference time may be assigned to the head-up display 143 displayed on the windshield 30.

Meanwhile, not only when the user gazes at the display located inside the vehicle 1, but also when the user gazes at the display located outside the vehicle 1, the user's eyes can be recognized and associated control corresponding to the user's eyes can be performed. A detailed description thereof will hereinafter be given with reference to FIGS. 23 to 27.

Figure 23:
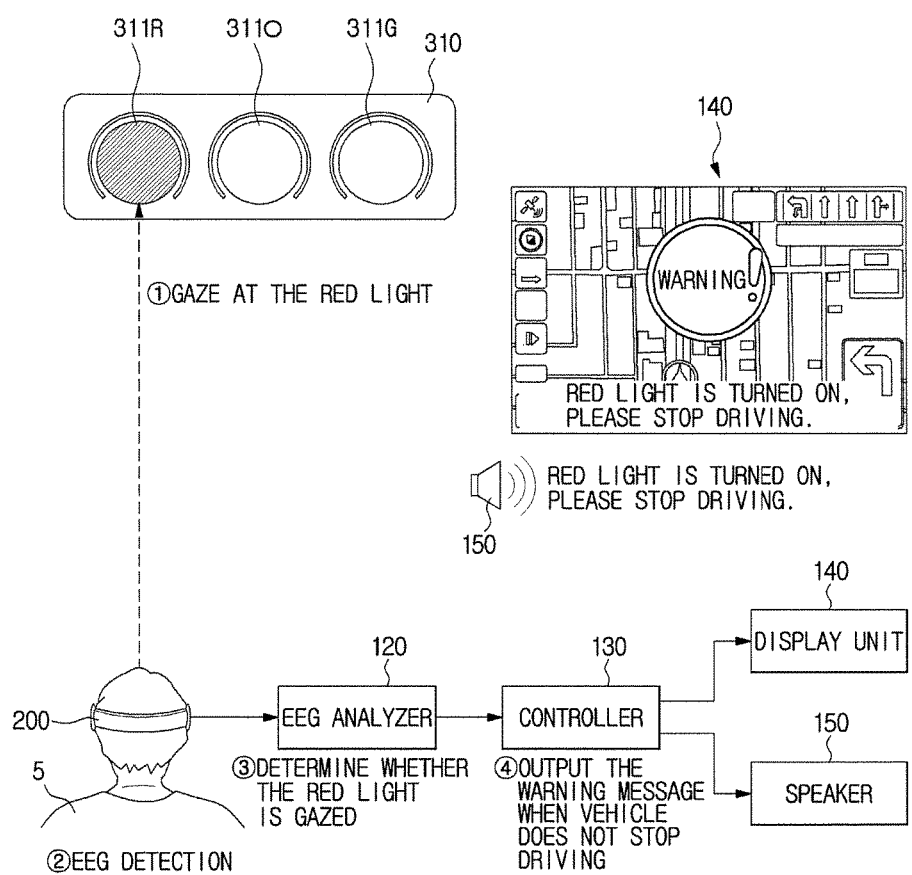
FIG. 23 is a conceptual diagram illustrating an example of a control operation for use in a case in which a user gazes at a red traffic light.
Figure 24:
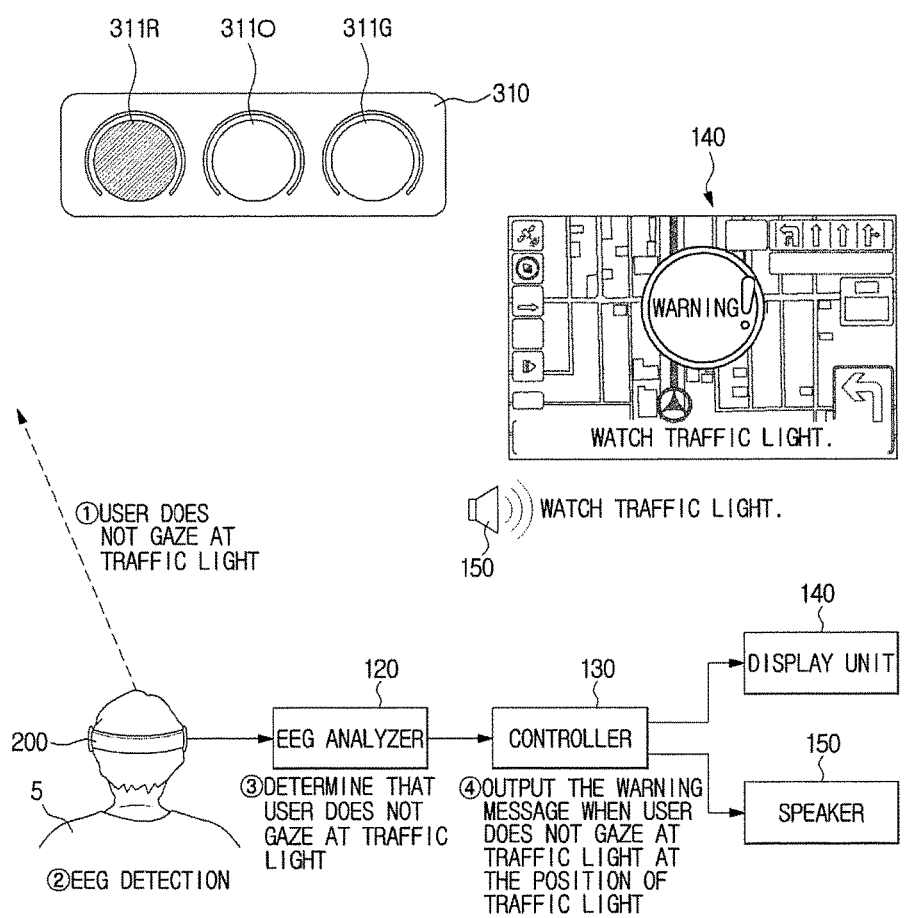
FIG. 24 is a conceptual diagram illustrating an example of a control operation for use in a case in which a user does not gaze at traffic lights.

FIG. 23 is a conceptual diagram illustrating an example of a control operation for use in a case in which a user gazes at a red traffic light. FIG. 24 is a conceptual diagram illustrating an example of a control operation for use in a case in which a user does not gaze at traffic lights.

Referring to FIG. 23, when the traffic light 310 located above the road displays a red light (311R), a yellow light (311O), and a green light (311G), a visual stimulus signal having a specific frequency may be inserted in the same manner as in the method for allowing the display unit 140 to insert the visual stimulus signal between visual information segments. For example, a visual stimulus signal of 15 Hz may be inserted into the red light (311R), a visual stimulus signal of 27 Hz may be inserted into the yellow light (311O), and a visual stimulus signal of 32 Hz may be inserted into the green light (311G). This frequency information may be stored in the storage 160. All the traffic lights located above the road may have the same frequency, or may have different frequencies according to installation positions. If the traffic lights have different frequencies according to installation positions, frequency information corresponding to the traffic light installed at a current position can be acquired using map data and vehicle position information.

Referring to FIG. 23, if the user gazes at the red light (311R), the EEG signal having the frequency of a visual stimulus signal displayed on the red light (311R) may occur in the occipital lobe. If the EEG detector detects the EEG signal of the user 5, the EEG analyzer 120 can determine the frequency by analyzing the detected EEG signal, and can also determine that the user 5 gazes at the red light on the basis of the determined frequency.

The controller 130 may determine whether the vehicle 1 stops driving. If the determined result indicates that the vehicle 1 does not stop driving although the user 5 gazes at the red light (311R), the controller 130 may provide the user 5 with the warning message through at least one of the display unit 140 and the speaker 150. For example, the warning message for instructing the vehicle driver to stop driving due to the red light may be displayed in a text form on the display unit 140, or the warning message may be output audibly through the speaker 150. If necessary, the sound-type warning message may be output alone or may be output simultaneously with the text-type warning message.

In addition, if an automatic brake system (ABS) is mounted to the vehicle 1, the vehicle 1 can also be automatically stopped.

In contrast, although the traffic light 310 is present, if the user 5 does not gaze at the traffic light 310, there is a possibility of causing unexpected traffic accidents. As shown in FIG. 24, if the user 5 does not gaze at the traffic light 310 at the installation position of the traffic light 310, the EEG signal having the frequency of a visual stimulus signal displayed on the red light (311R), the yellow light (311O) or the green light (311G) may not occur in the occipital lobe.

If the EEG detector 200 detects the EEG signal of the user 5, the EEG analyzer 120 may determine the frequency by analyzing the detected EEG signal, and may determine that the user does not gaze at the traffic light on the basis of the determined frequency. In this case, information as to whether the traffic light is located at the current position may be determined not only using vehicle position information received from a global positioning system (GPS) but also using map data stored in the storage 160. Position information of the traffic light may be contained in the map data.

If the user 5 does not gaze at the traffic light at the position of the traffic light, the controller 130 may display the warning message through at least one of the display unit 140 and the speaker 150. For example, the warning message for inviting the vehicle driver to view the traffic light may be displayed in a text form on the display unit 140, or the warning message may also be output audibly through the speaker 150. If necessary, the sound-type warning message may be output alone or may be output simultaneously with the text-type warning message.

Figure 25:
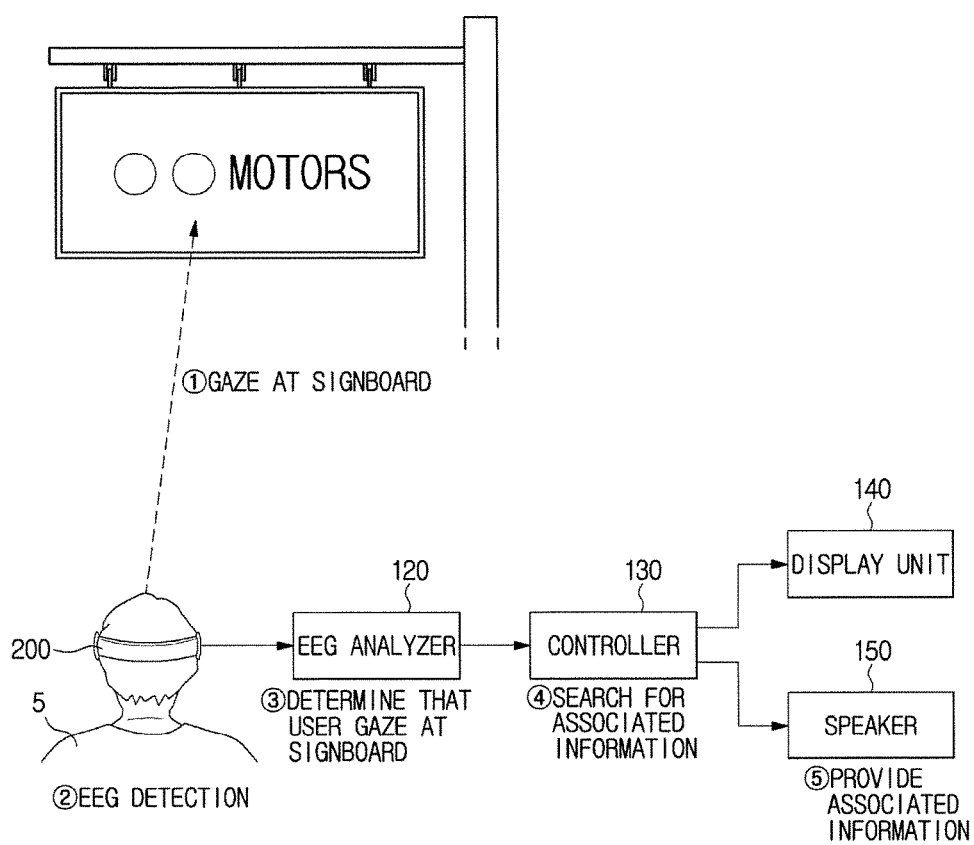
FIGS. 25 to 27 are conceptual diagrams illustrating exemplary control operations for use in a case in which a user gazes at a signboard located outside of a vehicle.
Figure 26:
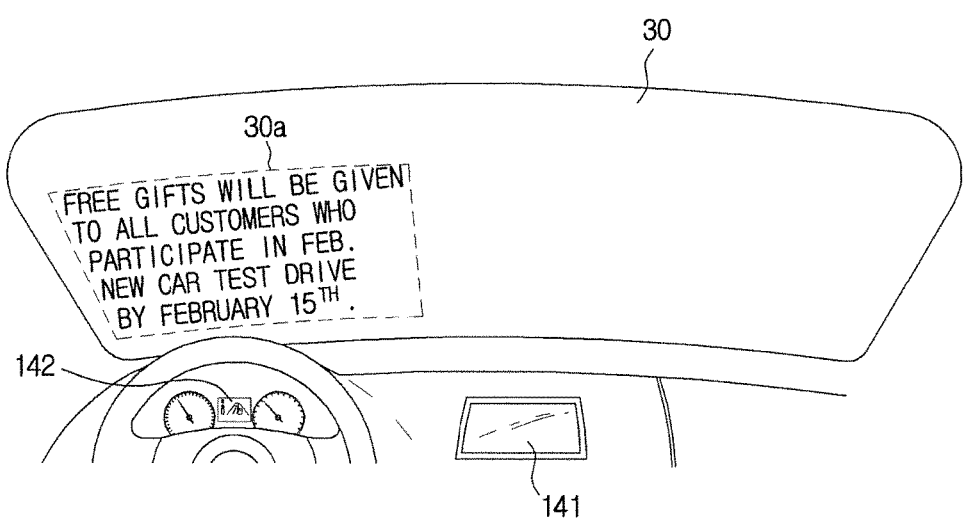
Figure 27:
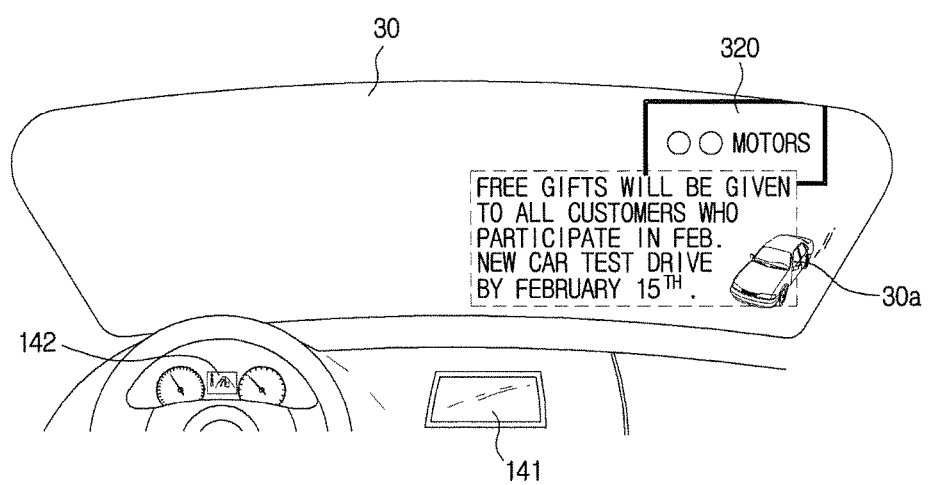

FIGS. 25 to 27 are conceptual diagrams illustrating exemplary control operations for use in a case in which a user gazes at a signboard located outside of a vehicle.

The user who drives the vehicle may view peripheral environments through the windshield 30 or other glasses mounted to the vehicle 1. The user who rides in the vehicle can view not only the traffic lights needed for vehicle driving but also advertisement display devices 320 (such as various signboards) located in the vicinity of the vehicle.

A visual stimulus signal having a specific frequency may be inserted into basic visual information displayed on the advertisement display device 320. In this case, the visual stimulus signal is displayed on the advertisement display device 320 instead of the vehicle 1, and the advertisement display device 320 may be an example of the above-mentioned display apparatus 100. In addition, the controller 130 of the vehicle 1 may not insert the visual stimulus signal into basic stimulus signal. However, the frequency of a visual stimulus signal displayed on the advertisement display device 320 may be pre-stored in the storage 160.

If the user 5 gazes at the advertisement display device 320, the EEG signal having the frequency of a visual stimulus signal displayed on the advertisement display device 320 may occur in the occipital lobe. If the EEG detector 220 detects the EEG signal of the user 5, the EEG analyzer 120 may determine the frequency by analyzing the detected EEG signal, and may determine that the user 5 gazes at the advertisement display device 320 on the basis of the determined frequency.

Associated information corresponding to respective advertisement display devices may be stored in the storage 160. The associated information stored in the storage 160 may be received from an enterprise (or company) of the corresponding advertisement display device 320. The controller 130 may search for associated information corresponding to the user-gazed advertisement display device 320, and may provide associated information through at least one of the display unit 140 and the speaker 150.

As can be seen from FIG. 25, if the user 5 gazes at the advertisement display device 320 of a specific car sales company, information associated with promotion of the specific car sales company can be provided. For example, as can be seen from FIG. 26, information associated with the new car test drive event may be displayed in a text form on the head-up display region 30a. Alternatively, as can be seen from FIG. 27, associated information may overlap with the advertisement display device 320 using the augmented reality technology, such that the overlap result can be displayed on the advertisement display device 320. Alternatively, although not shown in the drawings, associated information may also be displayed in a hologram form. That is, the scheme for providing information associated with the user-gazed advertisement display device is not limited.

Meanwhile, the warning message, information, or content may be displayed through the display unit 140 or the speaker 150 according to recognition of the user's eyes, and other functions of the vehicle may also be controlled according to recognition of the user's eyes. A detailed description thereof will hereinafter be given with reference to FIGS. 28 and 29.

Figure 28:
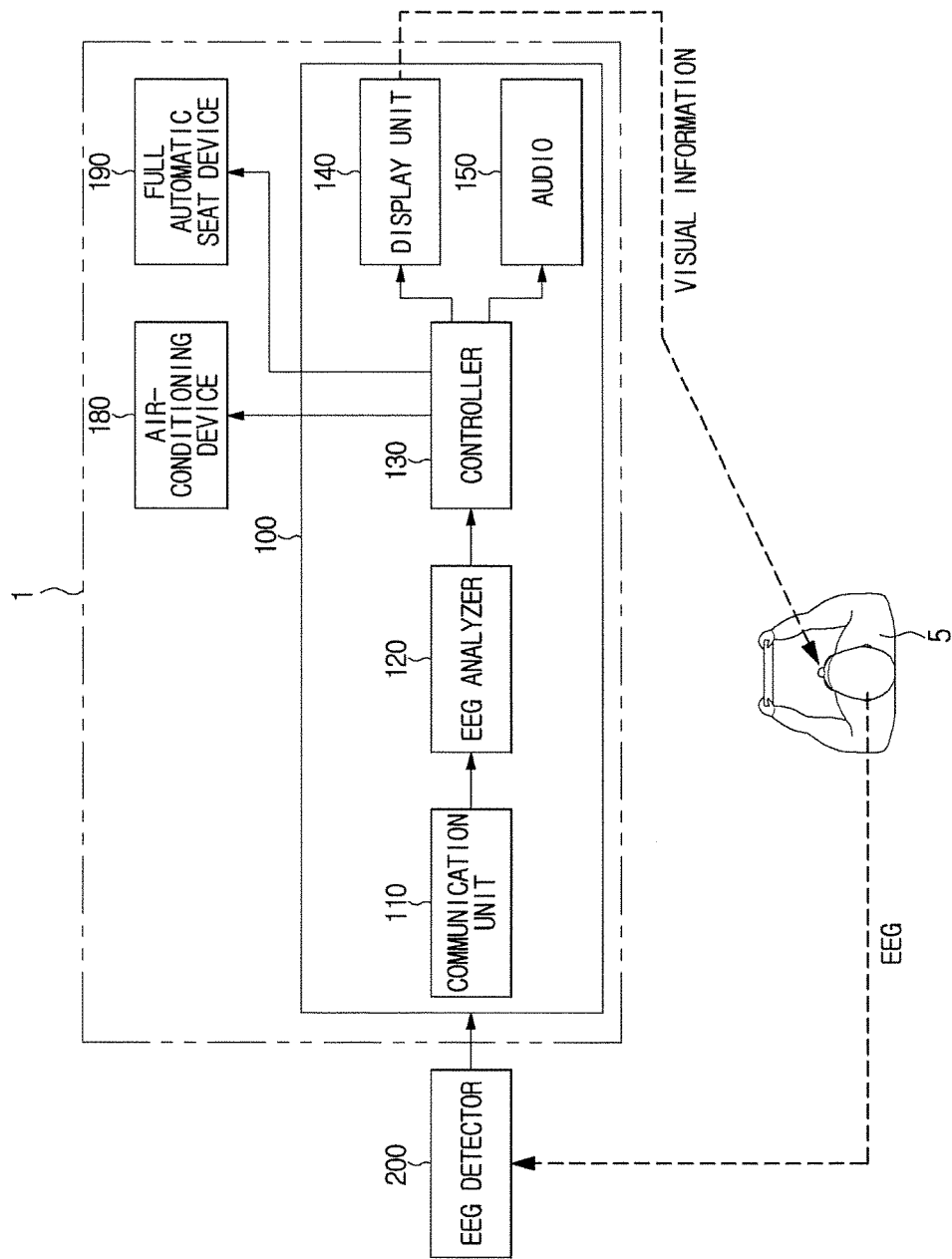
FIG. 28 is a block diagram illustrating a vehicle for controlling an air-conditioning device or a full automatic seat device by recognizing the user's eyes.
Figure 29:
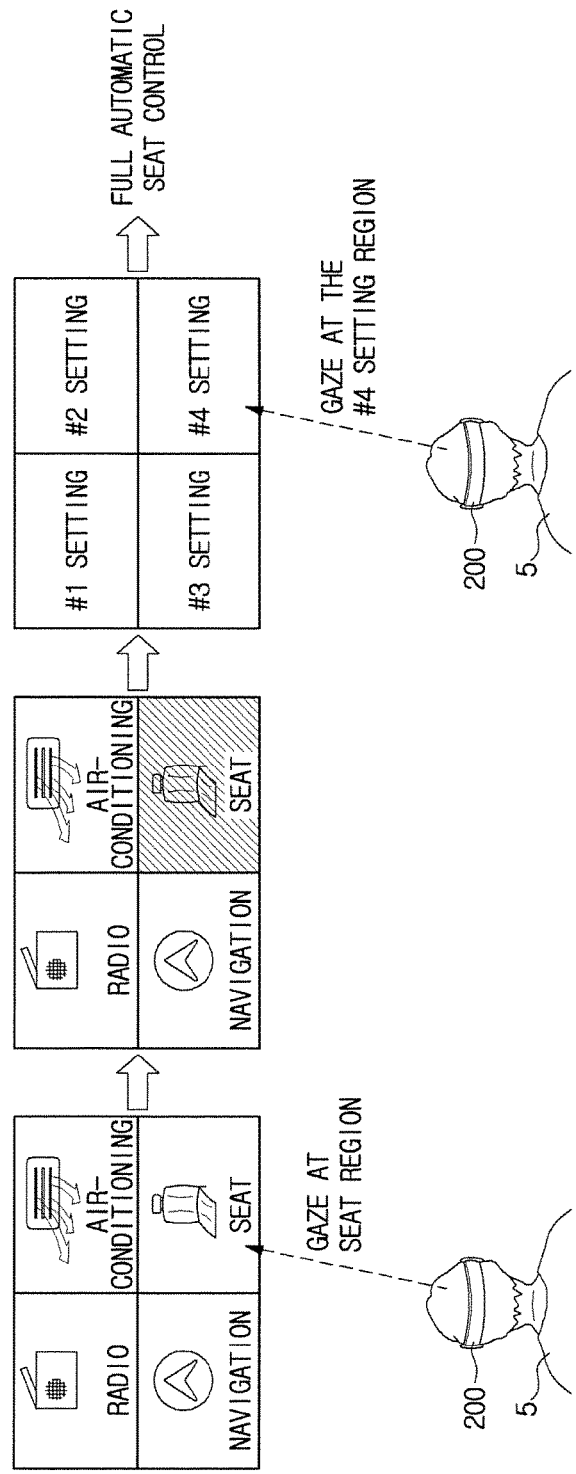
FIG. 29 exemplarily illustrates a screen image displayed on a display unit when an air-conditioning device or a full automatic seat device is controlled by recognizing the user's eyes.

FIG. 28 is a block diagram illustrating a vehicle for controlling an air-conditioning device or a full automatic seat device by recognizing the user's eyes. FIG. 29 exemplarily illustrates a screen image displayed on a display unit when an air-conditioning device or a full automatic seat device is controlled by recognizing the user's eyes.

Referring to FIG. 28, the vehicle 1 may further include an air-conditioning device 180 for adjusting air temperature of the internal space of the vehicle 1, and a full automatic seat device 190 for automatically adjusting the position of a vehicle seat. The controller 130 may control the air-conditioning device 180 and the full automatic seat device 190 according to the recognition result of the user's eyes.

Referring to FIG. 29, the AVN display 141 is divided into four regions ($R_1, R_2, R_3, R_4$), a radio function may be assigned to the first region ($R_1$), an air-conditioning function may be assigned to the second region ($R_2$), a navigation function may be assigned to the third region ($R_3$), and a seat control function may be assigned to the fourth region ($R_4$).

In order to discriminate which one of four regions is gazed at by the user 5, the visual stimulus signals having different frequencies may be displayed on four regions. In addition, if the user gazes at the radio region ($R_1$), visual information indicating selection of the radio function may be displayed on the radio region ($R_1$), and a visual stimulus signal may be inserted between frames constructing the visual information. If the user gazes at the air-conditioning region ($R_2$), visual information indicating selection of the air-conditioning control function may be displayed on the air-conditioning region ($R_2$), and a visual stimulus signal may be inserted between frames constructing the visual information. If the user gazes at the navigation region ($R_3$), visual information indicating selection of the navigation function may be displayed on the navigation region ($R_3$), and a visual stimulus signal may be inserted between frames constructing the visual information. If the user gazes at the seat control region ($R_4$), visual information indicating selection of the seat control function may be displayed on the seat control region ($R_4$), and a visual stimulus signal may be inserted between frames constructing the visual information.

If the user 5 gazes at the seat control region ($R_4$), the EEG signal having the frequency of a visual stimulus signal displayed on the seat control region ($R_4$) is generated. If the EEG detector 200 detects the EEG signal of the user 5, the EEG analyzer 120 analyzes the detected EEG signal so that it can determine that the user 5 gazes at the seat control region ($R_4$).

As shown in FIG. 29, the seat control region ($R_4$) may be shaded or denoted by bold lines, such that feedback to the user operation in which the user gazes at the seat control region ($R_4$) may be provided.

A setting value of the seat position may be pre-stored in the full automatic seat device 190. For example, if four setting values (i.e., #1 setting, #2 setting, #3 setting, and #4 setting) are pre-stored, a screen image in which one of the four setting values can be selected may be displayed on the AVN display 141. One screen image may be divided into four regions ($R_{41}, R_{42}, R_{43}, R_{44}$), and the four regions ($R_{41}, R_{42}, R_{43}, R_{44}$) may be respectively allocated to #1 setting, #2 setting, #3 setting, and #4 setting. The visual stimulus signals having different frequencies may be displayed on the respective regions. In this case, the method for inserting the visual stimulus signal between frames constructing the basic visual information may be used.

For example, if the user 5 gazes at the #4 setting region ($R_{44}$), the EEG signal having the frequency (i.e., the frequency corresponding to the #4 setting region ($R_{44}$)) of a visual stimulus signal displayed on the #4 setting region ($R_{44}$) may be generated. If the EEG detector 200 detects the EEG signal, the EEG analyzer 120 analyzes the detected EEG signal and determines the frequency on the basis of the analysis result. If the user 5 gazes at the #4 setting region ($R_{44}$) on the basis of the determined frequency, the controller 130 transmits a control signal to the full automatic seat device 190, so that the seat position of the user 5 can be adjusted according to the #4 setting value. In this case, the adjusted seat may be a driver seat (191FL) or a passenger seat (191FR), and information regarding selection indicating which seat will be controlled can be input prior to selection of the setting value.

Although not shown in the drawings, a region in which a temperature control function can be selected may be displayed on the display unit 140, and a visual stimulus signal having a specific frequency may be inserted into visual information displayed on the corresponding region. If the user 5 gazes at the corresponding region and the EEG signal having a specific frequency is generated, the controller 130 may adjust air temperature of the internal space of the vehicle by controlling the air-conditioning device 180. In this case, if it is determined that the user gazes at the corresponding region as shown in FIG. 15, the air-conditioning device 180 can be controlled according to user manipulation of the input unit, and a button for selecting a temperature of the corresponding region is configured so that recognition of the user's eyes can be mapped to temperature selection. In the latter case, such temperature control may be immediately adjusted to a user-desired temperature without additional manipulation of the input unit.

As described above, the above-mentioned display apparatus 100 inserts a visual stimulus signal having a specific frequency into basic visual information displayed on the display, measures the EEG signal having a specific frequency generated when the user gazes at the display, and determines the user intention, and the vehicle 1 including the display apparatus 100 has been disclosed. Specific functions and display screen images for use in the above-mentioned embodiment are disclosed only for illustrative purposes, and the scope or spirit of the display apparatus 100 and the vehicle 1 according to the embodiment is not limited thereto. Therefore, irrespective of the categories of functions executed by recognition of the user's eyes or the construction of a display screen image after decision of the user intention on the condition that a visual stimulus signal having a specific frequency is inserted into basic visual information displayed on the display, and the EEG signal having a specific frequency generated when the user gazes at the display is measured, the display apparatus 100 or the vehicle 1 according to the embodiment can also be applied to other examples without departing from the scope or spirit of the present invention.

A display method according to the embodiment will hereinafter be described. The display apparatus 100 or the vehicle 1 according to the embodiment may be used to perform the display method. Therefore, the above-mentioned description of the display apparatus 100 or the vehicle 1 may also be applied to the embodiment of the display method, and the following embodiment will exemplarily disclose a method for executing the display method using the vehicle 1 for convenience of description.

Figure 30:
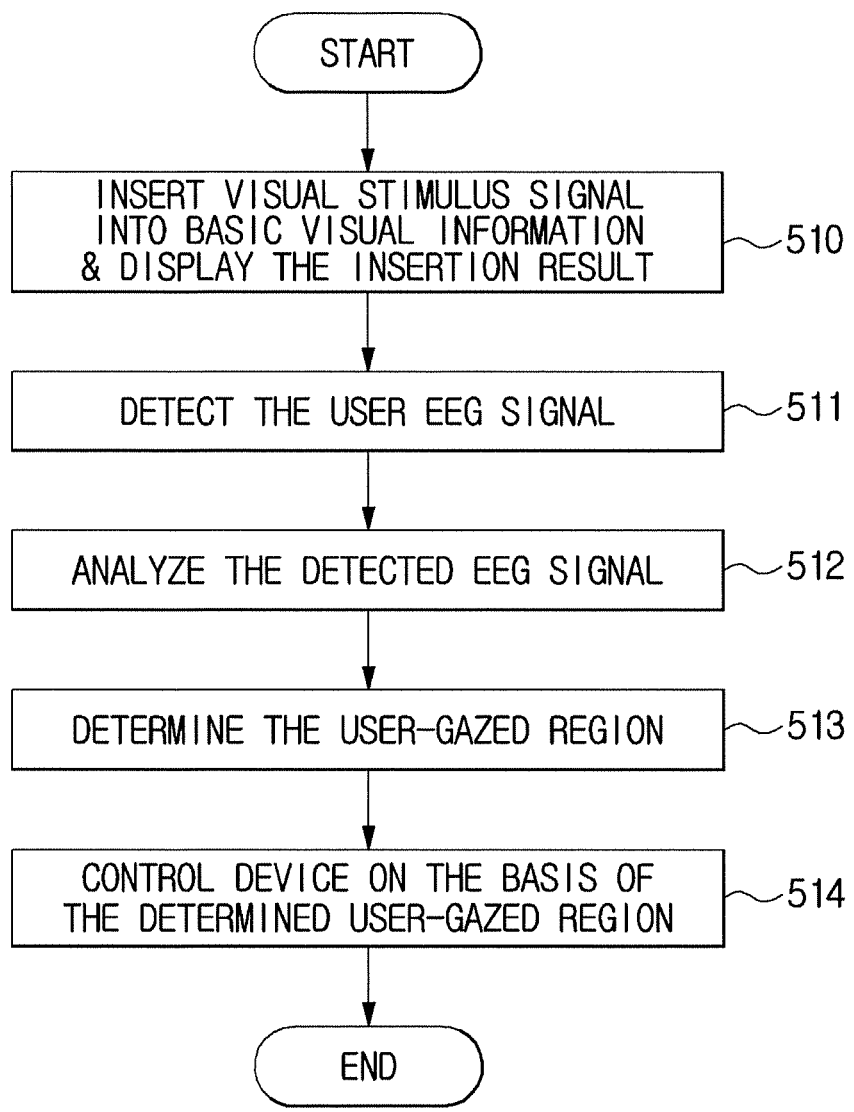
FIG. 30 is a flowchart illustrating a display method according to an embodiment of the present invention.

FIG. 30 is a flowchart illustrating a display method according to an embodiment of the present invention.

Referring to FIG. 30, a visual stimulus signal is inserted into basic visual information in operation 510. The basic visual information is displayed on the display unit 140 so as to provide the user with information or content. The EEG signal having a specific frequency is generated so that the resultant EEG signal is distinguished from the visual stimulus signal used for recognition of user intention. In addition, the basic visual information may be formed in moving images or in still images. If the basic visual information is formed in moving images, the visual stimulus signal may be inserted between frames constructing the moving images. If the basic visual information is formed in still images, the visual stimulus signal may be inserted into the process for displaying the still images. Alternatively, the still images may be displayed according to a predetermined frame rate in the same manner as in the moving images, and the visual stimulus signal may also be inserted between the still image frames.

The EEG signal of the user is detected using the EEG detector 200 in operation 511. If the user gazes at the visual stimulus signal having a specific frequency, the EEG signal having the same frequency as the specific frequency is generated. Therefore, a specific frequency component is contained in the EEG signal detected from the user who gazes at the visual stimulus signal.

The EEG analyzer 120 analyzes the detected EEG signal in operation 512, and determines the user-gazed region in operation 513. In more detail, the EEG analyzer 120 may discriminate the frequency component of the EEG signal through frequency analysis, and may determine the user-gazed region not only using a specific frequency pre-stored in the storage 160 but also using information regarding the region mapped to the specific frequency.

If a user-gazed region is determined, the device is controlled on the basis of the user-gazed region in operation 514. The user-gazed region and a control operation of the device corresponding to the user-gazed region may be mapped and stored in the storage 160. For example, if the user gazes at a specific region, information regarding a device to be controlled, and information regarding the device control method may be stored in the storage 160. If the user gazes at a specific region, a control signal is generated according to information stored in the storage 160, and the control signal can be transmitted to the corresponding device.

For example, a control target to be controlled by the input unit may be determined on the basis of the user-gazed region, a function corresponding to the user-gazed region may be immediately performed, and the construction of a display screen image may be controlled according to the use history information of the user. In addition, if the user 5 does not gaze at the traffic lights at the position of the traffic lights, or if it is determined that the vehicle does not stop driving although the red light is on, the warning message may be output through at least one of the display unit 140 and the speaker 150. In addition, if the user gazes at the display unit 140 for a predetermined reference time or more, this user gazing action for a long time may obstruct safe driving, such that the warning message for informing the user of this obstruction may be provided to the user.

Although EEG detection is implemented in the display method for convenience of description, the scope or spirit of the display method according to the embodiment is not limited to the EEG detection.

A detailed embodiment of the device control method will hereinafter be given in detail.

Figure 31:
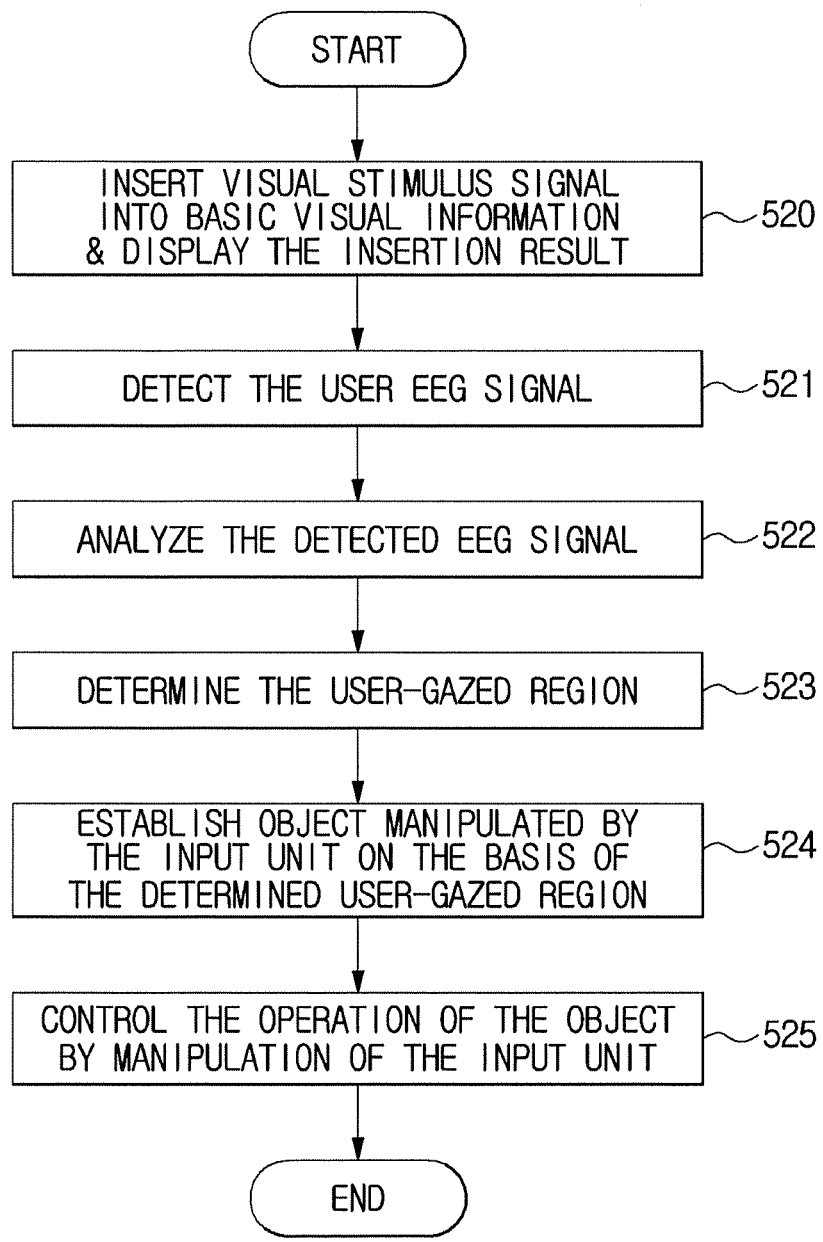
FIG. 31 is a flowchart illustrating a method for determining a control object by an input unit on the basis of a user-gazed region in the case of using a display method according to an embodiment of the present invention.

FIG. 31 is a flowchart illustrating a method for determining a control object by the input unit on the basis of a user-gazed region in the case of using a display method according to an embodiment of the present invention.

Referring to FIG. 31, a visual stimulus signal is inserted into basic visual information in operation 520. For example, the visual stimulus signal may be displayed on at least one of the AVN display 141, the cluster display 142, and the head-up display 143, and the visual stimulus signals displayed on respective displays may have different frequencies. In addition, as shown in FIG. 16, one display screen image is divided into a plurality of regions, and visual stimulus signals having different frequencies in respective regions may be displayed.

The EEG signal of the user is detected using the EEG detector 200 in operation 521. The EEG signal detected from the user who gazes at the visual stimulus signal may have a specific frequency component. Information regarding the specific frequency component may be pre-stored in the storage 160.

The EEG analyzer 120 analyzes the detected EEG signal in operation 522, and determines the user-gazed region in operation 523. In more detail, the EEG analyzer 120 may discriminate the frequency component of the EEG signal through frequency analysis, and may determine the user-gazed region not only using a specific frequency pre-stored in the storage 160 but also using information regarding the region mapped to the specific frequency.

A target object to be manipulated by the input unit is established on the basis of the determined user-gazed region in operation 524, and the operation of the target object is controlled by manipulation of the input unit in operation 525. For example, if the user rides in the vehicle 1, and if the user-gazed region is the AVN display 141, the AVN display 141 or the AVN terminal may be controlled by a control command entered by the user and received from the input unit. That is, if the user manipulates the input unit, the function or device corresponding to the user-gazed region may be controlled. In this case, the input unit to be manipulated by the user may be an arbitrary input unit. In this case, if the user gazes at the AVN display 141, although the user manipulates the cluster input unit 172, the AVN display 141 or the AVN terminal can be controlled. As a result, the input unit can be used for multiple purposes or usages, such that a plurality of input units mounted to the vehicle 1 is not used to control a specific function only, and a necessary input unit may be used to control a necessary function according to circumstance.

Figure 32:
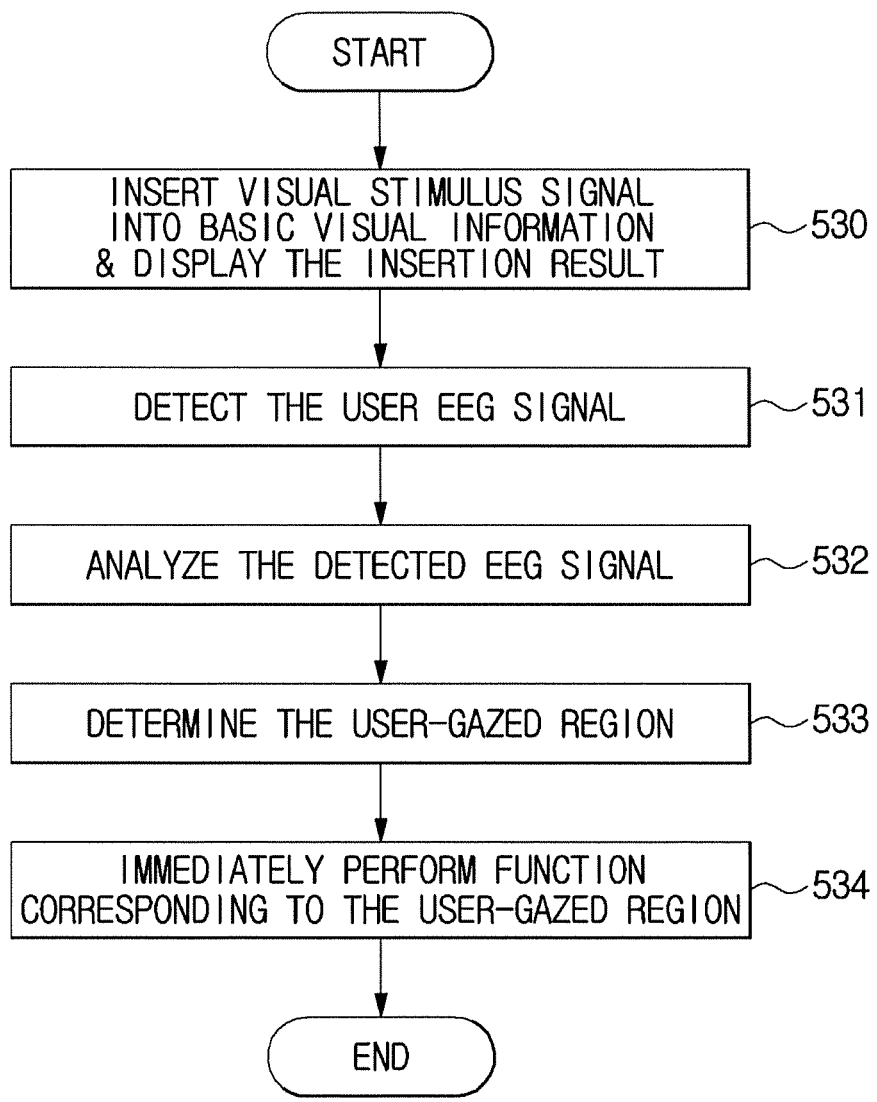
FIG. 32 is a flowchart illustrating a method for immediately executing a function corresponding to a user-gazed region in the case of using a display method according to an embodiment of the present invention.

FIG. 32 is a flowchart illustrating a method for immediately executing a function corresponding to a user-gazed region in the case of using a display method according to an embodiment of the present invention.

Referring to FIG. 32, a visual stimulus signal may be inserted into basic visual information in operation 530. The visual stimulus signal may be displayed on some regions of the display screen image as shown in FIG. 18 or FIG. 19, and visual stimulus signals having different frequencies corresponding to different shortcut functions may be displayed on some regions.

The EEG signal of the user is detected using the EEG detector 200 in operation 531. The EEG signal detected from the user who gazes at the visual stimulus signal may include the same frequency component as the frequency of a visual stimulus signal of the user-gazed region.

The EEG analyzer 120 analyzes the detected EEG signal in operation 532, and determines the user-gazed region in operation 533. In more detail, the EEG analyzer 120 may discriminate the frequency component of the EEG signal through frequency analysis, and may determine the user-gazed region not only using a specific frequency pre-stored in the storage 160 but also using information regarding the region mapped to the specific frequency.

In addition, a function corresponding to the user-gazed region is immediately carried out in operation 534. Although the above-mentioned embodiment has disclosed that, if the user gazes at a specific region, a function corresponding to the corresponding region can be controlled by manipulation of the input unit, the user operation of the user who gazes at the specific region may also be used as an input of the control command. As can be seen from the above-mentioned example, if the user gazes at the specific region, an end function, a navigation function, a radio function, a Bluetooth function, or a video function in response to a specific region may be immediately performed without additional manipulation of the input unit.

Figure 33:
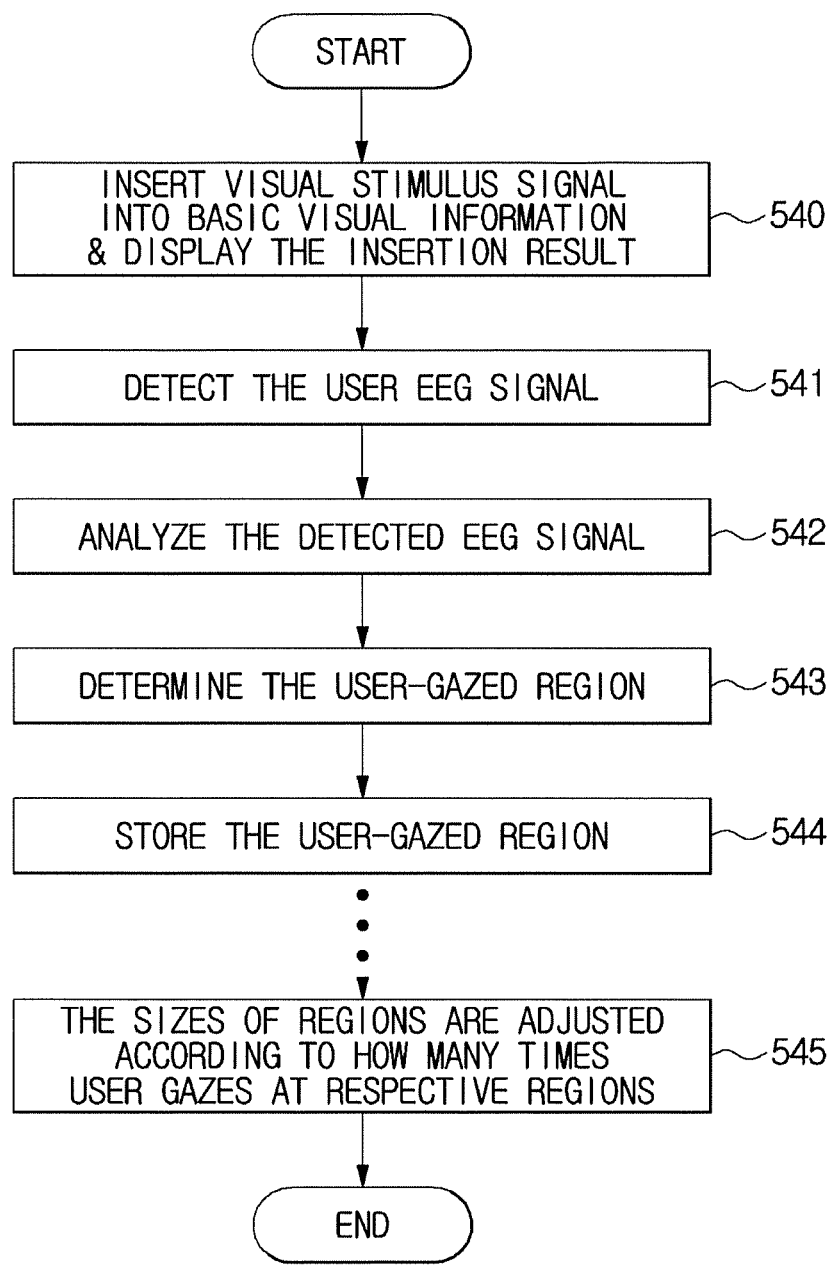
FIG. 33 is a flowchart illustrating a method for controlling constituent elements of a display screen image according to use history information of a user in the case of using a display method according to an embodiment of the present invention.

FIG. 33 is a flowchart illustrating a method for controlling constituent elements of a display screen image according to use history information of a user in the case of using a display method according to an embodiment of the present invention.

Referring to FIG. 33, a visual stimulus signal may be inserted into basic visual information and displayed in operation 540.

The EEG signal of the user is detected using the EEG detector 200 in operation 541. If the user gazes at the visual stimulus signal having a specific frequency, the EEG signal having the same frequency as a specific frequency is generated. The EEG signal detected from the user who gazes at the visual stimulus signal may include a specific frequency component.

The EEG analyzer 120 analyzes the detected EEG signal in operation 542, and determines the user-gazed region in operation 543. In more detail, the EEG analyzer 120 may discriminate the frequency component of the EEG signal through frequency analysis, and may determine the user-gazed region not only using the specific frequency pre-stored in the storage 160 but also using information regarding the region mapped to the specific frequency.

The user-gazed region is stored in the storage 160 in operation 544, such that a database (DB) regarding the use history of the user can be generated.

The operations 540 to 544 may be repeatedly performed. If the storing action of the user-gazed region is accumulated, a database (DB) for the use history is generated. As can be seen from FIG. 16, one display screen image is divided into a plurality of regions, and different functions are mapped to respective regions, such that the sizes of respective regions can be adjusted according to how many times the user gazes at the respective regions in operation 545. For example, as shown in FIG. 20, the region frequently gazed at by the user may be enlarged in size and displayed. For example, if the user frequently selects the radio function, the radio region (R1) may be enlarged in size and displayed, and the sizes of the remaining regions may be adjusted according to the order of user-selected frequency.

Figure 34:
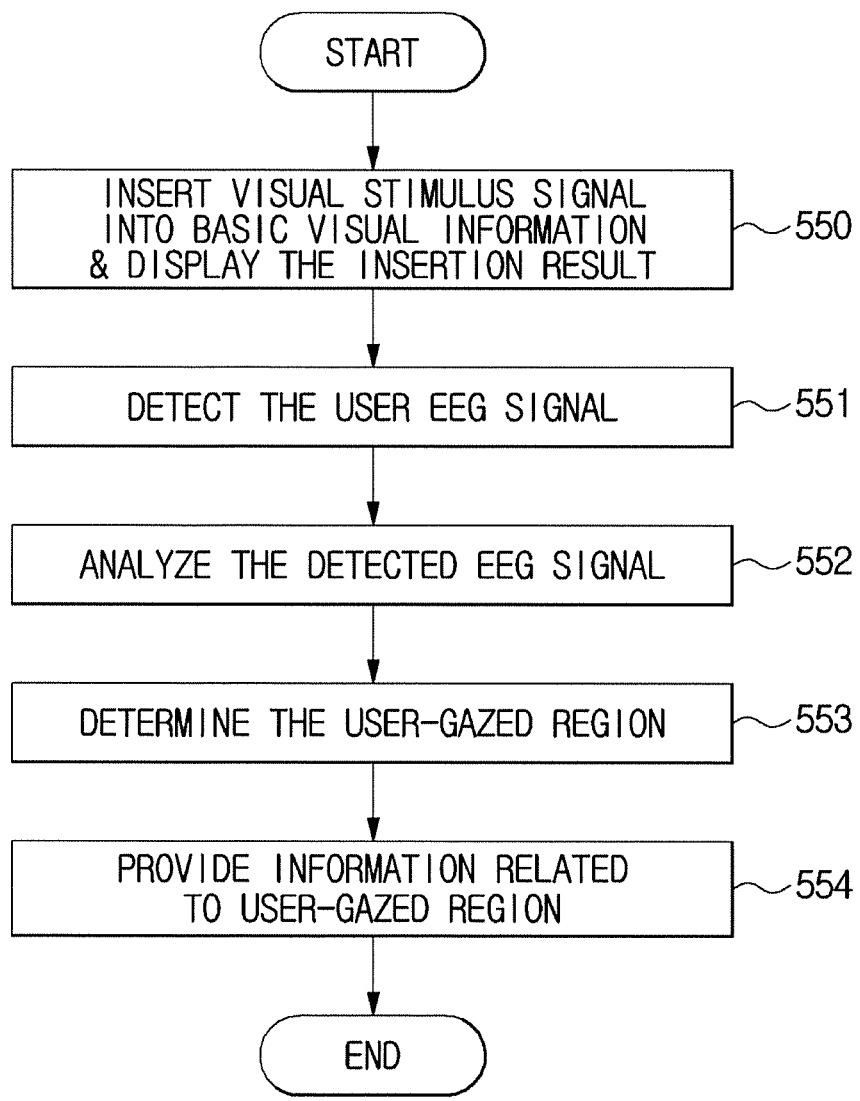
FIG. 34 is a flowchart illustrating a display method used when a user gazes at an external visual stimulus signal.

FIG. 34 is a flowchart illustrating a display method used when a user gazes at an external visual stimulus signal.

Referring to FIG. 34, a visual stimulus signal is inserted between basic visual information and displayed in operation 550. In this case, the display on which the basic visual information and the visual stimulus signal are displayed is not identical to the display installed into the vehicle, and may be the advertisement display device 320 such as various signboards located in a peripheral region. The frequency of the visual stimulus signal displayed on the advertisement display device 320 may be pre-stored in the storage 160.

The EEG signal of the user is detected in operation 551, the detected EEG signal is analyzed in operation 552, and the user-gazed region is determined in operation 553.

Associated information corresponding to respective advertisement display devices may be stored in the storage 160. The stored associated information may be received from an enterprise or company of the advertisement display device 320. The controller 130 may search for associated information corresponding to the advertisement display device 320 gazed at by the user 5, and may provide associated information through at least one of the display unit 140 and the speaker 150 in operation 554. If associated information is provided through the display unit 140, the associated information may be displayed in text form, or the associated information may overlap with the advertisement display device 320 using augmented reality technology, such that the overlap result can be displayed on the advertisement display device 320.

Figure 35:
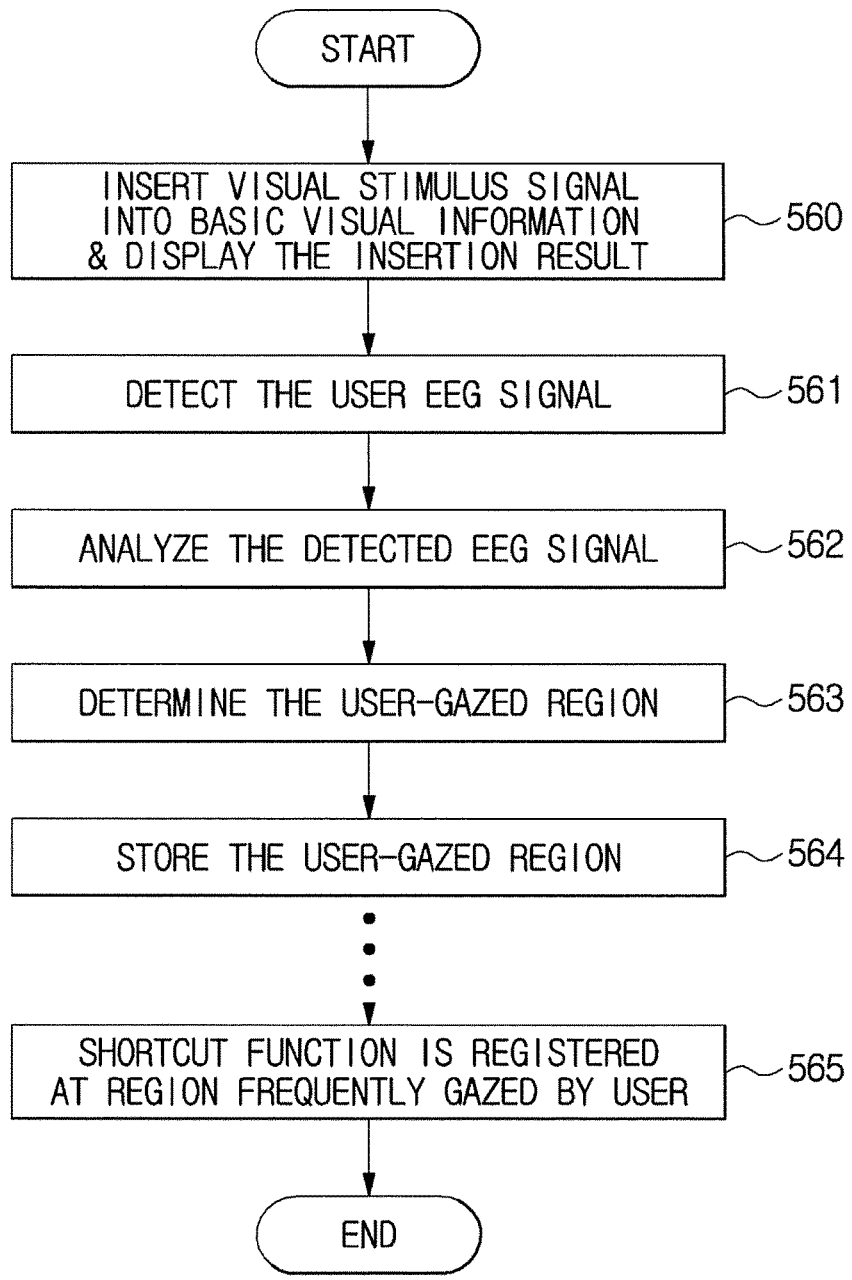
FIG. 35 is a flowchart illustrating another method for controlling constituent elements of a display screen image based on use history information of a user.

FIG. 35 is a flowchart illustrating another method for controlling constituent elements of a display screen image based on use history information of a user.

Referring to FIG. 35, a visual stimulus signal is inserted into basic visual information and displayed in operation 560, and the user EEG signal is detected using the EEG detector 200 in operation 561. The EEG analyzer 120 analyzes the detected EEG signal in operation 562, and determines the user-gazed region in operation 563. The user-gazed region is stored in the storage 160 in operation 564.

The above-mentioned operations 560 to 564 may be repeatedly performed. If the storing action of the user-gazed region is accumulated, a database (DB) regarding the use history may be generated.

The examples shown in FIGS. 18, 19, and 32 have disclosed that, if the user gazes at a specific region, a function corresponding to the specific region can be immediately performed. A function immediately performed by the user gazing action may be registered on the basis of the DB related to the use history. For example, a function corresponding to the region frequently gazed at by the user may be registered as a shortcut function in operation 565.

Meanwhile, the DB related to the use history may include not only the use history determined on the basis of the action of the user who gazes at a specific region, but also the use history determined on the basis of a control command received from the input unit.

In addition, the use history information may be used to display the above-mentioned user-adaptive screen image within one vehicle 1. If the use history information is collected from several vehicles used by several users, the collected history information may be used as big data utilized for customer research or marketing research.

The display device, the vehicle and the display method according to the embodiments of the present invention can insert a visual stimulus signal having a specific frequency into basic visual information so as to recognize the user's eyes, and can reduce eye fatigue of the user and can enable efficient use of the display.

In addition, the user intention is recognized by recognition of the user's eyes, and the recognized user intention is used to control the device, such that convenience of a user who manipulates the input unit can increase and vehicle safety can be guaranteed.

As is apparent from the above description, the display apparatus, the vehicle, and the display method according to the embodiments can recognize the user's intention by recognizing the user's eyes, and can apply the recognized result to a device control process, resulting in increased convenience of the user who manipulates the input unit.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. A display apparatus comprising:
   a controller configured to interpose a visual stimulus signal having a predetermined frequency between immediately adjacent basic visual information frames which do not contain the visual stimulus signal;
   a display unit configured to display the visual stimulus signal for generating an electroencephalogram (EEG) signal and the basic visual information frames; and
   an electroencephalogram (EEG) analyzer configured to determine a frequency occupied by the generated EEG signal.

2. The display apparatus according to claim 1, wherein the EEG signal generated by the visual stimulus signal includes a steady-state visual evoked potential (SSVEP).

3. The display apparatus according to claim 1, wherein the display unit displays the basic visual information frames in a form of moving images or still images.

4. The display apparatus according to claim 1, further comprising:
   a communication unit configured to receive the generated EEG signal from an electroencephalogram detector for detecting the EEG signal of a user.

5. The display apparatus according to claim 4, wherein the EEG analyzer recognizes the user's eyes on the basis of the frequency occupied by the generated EEG signal.

6. The display apparatus according to claim 1, wherein the controller generates a control signal to activate a function corresponding to the frequency occupied by the generated EEG signal.

7. The display apparatus according to claim 1, wherein the controller divides a screen image of the display unit into a plurality of regions, and inserts visual stimulus signals having different frequencies into basic visual information frames displayed on the divided regions.

8. A vehicle comprising:
   a controller configured to interpose a visual stimulus signal between immediately adjacent basic visual information frames which do not contain the visual stimulus signal;
   a display unit configured to display the visual stimulus signal for generating an electroencephalogram (EEG) signal and the basic visual information frames;
   a communication unit configured to receive an EEG signal from an EEG detector for detecting an EEG signal of a user; and
   an electroencephalogram (EEG) analyzer configured to determine a frequency occupied by the EEG signal of the user, and determine a region gazed by the user on the basis of the determined frequency.

9. The vehicle according to claim 8, wherein the electroencephalogram (EEG) signal generated by the visual stimulus signal includes a steady-state visual evoked potential (SSVEP).

10. The vehicle according to claim 9, wherein the display unit includes a plurality of displays.

11. The vehicle according to claim 10, wherein the controller inserts visual stimulus signals having different frequencies into basic visual information frames respectively displayed on the plurality of displays.

12. The vehicle according to claim 11, wherein the controller controls a function related to the display gazed by the user from among the plurality of displays.

13. The vehicle according to claim 12, further comprising:
an input unit configured to receive a control command from the user,
wherein the controller controls a function related to the user-gazed display according to a control command received from the input unit manipulated by the user.

14. The vehicle according to claim 8, wherein the controller inserts different visual stimulus signals into different visual information displayed on different regions of the display unit.

15. The vehicle according to claim 14, wherein the controller, if the user gazes at one of the regions of the display unit, immediately executes a function corresponding to the one of the regions, such that the immediately executed function is determined to be a shortcut function.

16. The vehicle according to claim 15, wherein the controller determines the function frequently used by the user or the function frequently gazed by the user to be the shortcut function.

17. The vehicle according to claim 8, further comprising:
a speaker configured to output an acoustic or sound signal.

18. The vehicle according to claim 17, wherein the controller, if the user gazes at the display unit during a predetermined reference time or more, outputs a warning message through at least one of the display unit and the speaker.

19. The vehicle according to claim 17, wherein the controller, if the user does not gaze at traffic lights, outputs a warning message through at least one of the display unit and the speaker.

20. The vehicle according to claim 17, wherein the controller, if the user gazes at a red light from among traffic lights, and if the vehicle does not stop driving, outputs a warning message through at least one of the display unit and the speaker.

21. The vehicle according to claim 8, wherein the display unit enlarges a display size of a region corresponding to a function frequently used by the user or a display size of a region frequently gazed by the user.

22. The vehicle according to claim 8, wherein the display unit includes an Audio Video Navigation (AVN) display, a cluster display, and a head-up display.

23. A display apparatus comprising:
a controller configured to interpose a visual stimulus signal between immediately adjacent basic visual information frames which do not contain the visual stimulus signal; and
a display unit configured to display the visual stimulus signal for generating an electroencephalogram (EEG) signal and the basic visual information frames.

24. A display method comprising:
interposing a visual stimulus signal between immediately adjacent basic visual information frames which do not contain the visual stimulus signal;
receiving an electroencephalogram (EEG) signal of a user;
determining a region gazed by the user by analyzing the received EEG signal; and
performing a control function corresponding to the user-gazed region.

25. The display method according to claim 24, wherein the determining the user-gazed region includes:
determining a frequency occupied by the received EEG signal; and
determining whether the determined frequency is identical to the predetermined frequency of the visual stimulus signal.

26. The display method according to claim 24, further comprising:
mapping a region on which the visual stimulus signal is displayed to a control function corresponding to the region, and storing the mapped result.

* * * * *